US011725189B2

(12) United States Patent
Iwao et al.

(10) Patent No.: US 11,725,189 B2
(45) Date of Patent: Aug. 15, 2023

(54) MAINTENANCE CULTURE OF INDUCED PLURIPOTENT STEM CELL-DERIVED INTESTINAL STEM CELLS

(71) Applicants: PUBLIC UNIVERSITY CORPORATION NAGOYA CITY UNIVERSITY, Nagoya (JP); FUJIFILM Corporation, Tokyo (JP)

(72) Inventors: Takahiro Iwao, Nagoya (JP); Tamihide Matsunaga, Nagoya (JP); Satoshi Kondo, Nagoya (JP); Shota Mizuno, Nagoya (JP)

(73) Assignees: PUBLIC UNIVERSITY CORPORATION NAGOYA CITY UNIVERSITY, Nagoya (JP); FUJIFILM Corporation, Tokyo (JP)

( * ) Notice: Subject to any disclaimer, the term of this patent is extended or adjusted under 35 U.S.C. 154(b) by 889 days.

(21) Appl. No.: 16/544,993

(22) Filed: Aug. 20, 2019

(65) Prior Publication Data
US 2020/0002680 A1    Jan. 2, 2020

Related U.S. Application Data

(63) Continuation of application No. PCT/JP2018/005849, filed on Feb. 20, 2018.

(30) Foreign Application Priority Data

Feb. 20, 2017   (JP) ................................ 2017-029448

(51) Int. Cl.
*C12N 5/071* (2010.01)
*G01N 33/50* (2006.01)

(52) U.S. Cl.
CPC ....... *C12N 5/0679* (2013.01); *G01N 33/5014* (2013.01); *G01N 33/5044* (2013.01); *C12N 2501/115* (2013.01); *C12N 2501/119* (2013.01); *C12N 2501/415* (2013.01); *C12N 2501/999* (2013.01); *C12N 2506/45* (2013.01)

(58) Field of Classification Search
CPC .................................................. C12N 5/0679
See application file for complete search history.

(56) References Cited

U.S. PATENT DOCUMENTS

| | | |
|---|---|---|
| 2012/0196312 A1 | 8/2012 | Sato et al. |
| 2014/0199700 A1 | 7/2014 | Kume et al. |
| 2014/0243227 A1 | 8/2014 | Clevers et al. |
| 2015/0361392 A1 | 12/2015 | Biehs |
| 2016/0194604 A1 | 7/2016 | Karp et al. |
| 2019/0079076 A1 | 3/2019 | Iwao et al. |
| 2019/0390171 A1 | 12/2019 | Sato et al. |

FOREIGN PATENT DOCUMENTS

| | | | |
|---|---|---|---|
| CN | 105358677 A | 2/2016 | |
| JP | 2014-516562 A | 7/2014 | |
| JP | 2016-512958 A | 5/2016 | |
| KR | 10-2013-0101557 A | 9/2013 | |
| WO | 2012/060315 A1 | 5/2012 | |
| WO | 2014/132933 A1 | 9/2014 | |
| WO | WO-2014132933 A1 * | 9/2014 | ........... C12N 5/0679 |
| WO | 2014/159356 A1 | 10/2014 | |
| WO | WO-2016123474 A1 * | 8/2016 | ........... C12N 5/0679 |
| WO | 2017/154795 A1 | 9/2017 | |
| WO | 2017/199811 A1 | 11/2017 | |

OTHER PUBLICATIONS

Lugli et al. (2016, EMBO reports, vol. 17(5), pp. 769-779). (Year: 2016).*
Yin et al. (2014, Nat. Methods, vol. 11(1), pp. 106-112). (Year: 2014).*
Xiaolei Yin et al., "Niche-independent high-purity cultures of Lgr5+ intestinal stem cells and their progeny", Nature Methods, Jan. 2014, vol. 11, No. 1, pp. 106-112 (20 pages total).
Xia Wang et al., "Cloning and variation of ground state intestinal stem cells", Nature, Jun. 11, 2015, vol. 522, pp. 173-178 (18 pages total).
Toshiro Sato et al., "Long-term Expansion of Epithelial Organoids From Human Colon, Adenoma, Adenocarcinoma, and Barrett's Epithelium", Gastroenterology, Nov. 2011, vol. 141, No. 5, pp. 1762-1772.
Tatsuya Ozawa et al., "Generation of enterocyte-like cells from human induced pluripotent stem cells for drug absorption and metabolism studies in human small intestine", Scientific Reports, Nov. 12, 2015, vol. 5, No. 16479, pp. 1-11.
Takahiro Iwao et al., Generation of Enterocyte-Like Cells with Pharmacokinetic Functions from Human Induced Pluripotent Stem Cells Using Small-Molecule Compounds, Drug Metab. Dispos., Apr. 2015, vol. 43, pp. 603-610.
International Search Report dated May 22, 2018, issued by the International Searching Authority in corresponding application No. PCT/JP2018/005849.
Written Opinion dated May 22, 2018, issued by the International Searching Authority in corresponding application No. PCT/JP2018/005849.

(Continued)

*Primary Examiner* — Anoop K Singh
*Assistant Examiner* — David A Montanari
(74) *Attorney, Agent, or Firm* — Sughrue Mion, PLLC

(57) ABSTRACT

It is an object to provide a culture method which is capable of maintaining and/or culturing iPS cell-derived intestinal stem cells, while maintaining the properties of intestinal stem cells. The induced pluripotent stem cell-derived intestinal stem cell-like cells are cultured in the presence of a GSK-3β inhibitor, a histone deacetylation inhibitor, and a serum replacement, or in the presence of a GSK-3β inhibitor and a serum replacement. Preferably, the culture is carried out under conditions in which one or more compounds selected from the group consisting of an epidermal growth factor, a TGFβ receptor inhibitor and a fibroblast growth factor are further present.

10 Claims, 5 Drawing Sheets

(56) References Cited

OTHER PUBLICATIONS

International Preliminary Report on Patentability dated Aug. 20, 2019, issued by the International Bureau in corresponding application No. PCT/JP2018/005849.
Office Action dated Feb. 1, 2021 from the Korean Intellectual Property Office in KR Application No. 10-2019-7024160.
Office Action dated Feb. 2, 2021 from the Japanese Patent Office in JP Application No. 2018-568660.
Office Action dated Jun. 18, 2020 from the Korean Intellectual Property Office in Korean Application No. 10-2019-7024160.
Office Action dated Jun. 30, 2020 from the Japanese Patent Office in Japanese Application No. 2018-568660.
Office Action dated May 25, 2021, from the Canadian Intellectual Property Office in Canadian application No. 3,053,893.
Office Action dated Mar. 5, 2021 in European Application No. 18755030.6.
Office Action dated Mar. 12, 2021 in Korean Application No. 10-2021-7006315.
Office Action dated Jul. 6, 2020 from the Canadian Patent Office in Canadian Application No. 3,053,893.
Takahiro Iwao et al., "Differentiation of Human Induced Pluripotent Stem Cells into Functional Enterocyte-like Cells Using a Simple Method", Drug Metabolism and Pharmacokinetics, vol. 29, No. 1, 2014, pp. 44-51 (8 pages total).
Heather K. Bone et al., "A novel chemically directed route for the generation of definitive endoderm from human embryonic stem cells based on inhibition of GSK-3", Journal of Cell Science, vol. 124, No. 12, 2011, pp. 1992-2000 (9 pages total).
Extended European Search Report (EESR) dated Feb. 7, 2020, from the European Patent Office in European Application No. 18755030.6.
Jason R. Spence et al., "Directed differentiation of human pluripotent stem cells into intestinal tissue in vitro", Nature, Feb. 3, 2011, vol. 470, pp. 105-109 (6 pages total).
Office Action dated Aug. 31, 2022 issued in Chinese Application No. 201880012849.7.
Office Action dated May 11, 2023 from the Chinese Patent Office in Chinese Application No. 201880012849.7.

\* cited by examiner

MAINTENANCE CULTURE OF INDUCED PLURIPOTENT STEM CELL-DERIVED INTESTINAL STEM CELLS

CROSS-REFERENCE TO RELATED APPLICATIONS

This application is a Continuation of PCT International Application No. PCT/JP2018/005849 filed on Feb. 20, 2018, which claims priority under 35 U.S.C. § 0119(a) to Japanese Patent Application No. 2017-029448 filed on Feb. 20, 2017. Each of the above application(s) is hereby expressly incorporated by reference, in its entirety, into the present application.

TECHNICAL FIELD

The present invention relates to a technique of culturing induced pluripotent stem cell-derived intestinal stem cells and intended use thereof. The present application claims priority from Japanese Patent Application No. 2017-029448, filed on Feb. 20, 2017; all the disclosure of which is hereby incorporated by reference.

BACKGROUND ART

Since many drug-metabolizing enzymes or drug transporters are present in the small intestine, the small intestine is, as with the liver, extremely important as an organ associated with first-pass effect of drugs. Thus, evaluation of the membrane permeability or metabolism of a pharmaceutical product in the small intestine from the initial stage of the development of the pharmaceutical product is necessary for the development of a pharmaceutical product excellent in pharmacokinetic properties. At present, as a small intestine model system, human colon cancer-derived Caco-2 cells have been frequently used. However, the expression pattern of a drug transporter in Caco-2 cells is different from that in human small intestine. In addition, since the expression of a drug-metabolizing enzyme and enzyme induction are hardly observed in the Caco-2 cells, it is difficult to accurately evaluate pharmacokinetics in the small intestine, using the Caco-2 cells. Accordingly, in order to comprehensively evaluate drug metabolism and membrane permeability in the small intestine, the use of primary small intestinal epithelial cells is desirable, but it is difficult to acquire such primary small intestinal epithelial cells.

Under such circumstances, the use of intestinal epithelial cells produced from human induced pluripotent stem cells (iPS cells) having the same pluripotency as that of human embryonic stem cells (ES cells) and almost infinite proliferative ability has been anticipated.

Several techniques of isolating intestinal stem cells from the intestinal tract of a living body and then culturing the intestinal stem cells or intestinal epithelial cells in vitro, or several techniques of inducing differentiation of intestinal epithelial cells from human iPS cells have been reported (see, for example, Patent Documents 1 to 4 and Non-Patent Documents 1 to 3), but there are no reports regarding a culture technique for the purpose of maintenance or proliferation of human iPS cell-derived intestinal stem cells.

PRIOR ART DOCUMENTS

Patent Documents

Patent Document 1: International Publication WO 2014/132933
Patent Document 2: JP 2016-512958 A
Patent Document 3: JP 2014-516562 A
Patent Document 4: Re-Publication of PCT International Application No. 2012-060315

Non-Patent Documents

Non-Patent Document 1: Yin X. et al., Niche-independent high-purity cultures of Lgr5(+) intestinal stem cells and their progeny. Nature Methods, 2014, 11(1): pp. 106-112.
Non-Patent Document 2: Wang X, et al., Cloning and Variation of Ground State Intestinal Stem Cells. Nature, 522 (7555): 173-178. (2015)
Non-Patent Document 3: Sato T. et al., Long-term expansion of epithelial organoids from human colon, adenoma, adenocarcinoma, and Barrett's epithelium, Gastroenterology. 2011 November; 141(5): 1762-72

SUMMARY OF INVENTION

Object to be Solved by the Invention

Differentiation of iPS cells into intestinal epithelial cells is problematic in that it requires enormous time and costs. In addition, in order to supply large quantities of human iPS cell-derived intestinal epithelial cells, it is essential to develop a culture technique at the stage of intestinal stem cells during differentiation. Hence, it is an object of the present invention to provide a culture technique capable of maintaining and/or culturing iPS cell-derived intestinal stem cells, while maintaining the properties of intestinal stem cells, namely, undifferentiation property, proliferative ability and differentiation ability to differentiate into intestinal epithelial cells, and the application and/or intended use thereof.

Means for Solving the Object

While taking into consideration the previous reports, the present inventors have conceived of various combinations of factors that seem to be necessary or effective for the maintenance of undifferentiation property, and have studied, in detail, the effects and/or influence of such factors on the culture of intestinal stem cell-like cells induced from human iPS cells. As a result, the present inventors have found a combination of particularly effective factors, and by using a culture solution, in which such a combination is used, it has become possible to maintain human iPS-derived intestinal stem cell-like cells and/or allow them to grow, while maintaining the properties of the cells. Moreover, when the intestinal stem cell-like cells maintained by the present culture method were induced to differentiate into intestinal epithelial cells, surprisingly, the expression of an intestinal epithelial marker and a pharmacokinetics-related gene was significantly increased, in comparison to a case where the cells had not been cultured according to the present culture method. That is to say, it has been revealed that the successfully established culture method does not only enable mass preparation of intestinal stem cell-like cells or long-term maintenance thereof, but it is also useful for promotion of differentiation of the cells into intestinal epithelial cells and the improvement of the functions thereof. The following inventions are principally based on the aforementioned results.

[1] A method for culturing induced pluripotent stem cell-derived intestinal stem cell-like cells, which comprises a step of culturing induced pluripotent stem cell-derived intestinal stem cell-like cells in the presence of a GSK-3β inhibitor, a histone deacetylation inhibitor, and a serum replacement, or in the presence of a GSK-3β inhibitor and a serum replacement.

[2] The method according to the above [1], wherein the GSK-3β inhibitor is CHIR 99021, SB216763, CHM 98014, TWS119, Tideglusib, SB415286, BIO, AZD2858, AZD1080, AR-A014418, TDZD-8, LY2090314, IM-12, Bikinin or 1-Azakenpaullone, the histone deacetylation inhibitor is valproic acid, vorinostat, trichostatin A, tubastatin A, givinostat or pracinostat, and the serum replacement is a knockout serum replacement.

[3] The method according to the above [1] or [2], wherein the culture is carried out under conditions in which one or more compounds selected turn the group consisting of an epidermal growth factor, a TGFβ receptor inhibitor and a fibroblast growth factor are further present.

[4] The method according to the above [3], wherein the TGFβ receptor inhibitor is A-83-01, and the fibroblast growth factor is FGF2, FGF4 or FGF10.

[5] The method according to any one of the above [1] to [4], wherein the culture is carried out under conditions in which one or more compounds selected from the group consisting of a BMP inhibitor, a Wnt signaling activator and a Wnt agonist are further present.

[6] The method according to the above [5], wherein the BMP inhibitor is Noggin, the Wnt signaling activator is R-spondin 1, and the Wnt agonist is Wnt3a.

[7] The method according to any one of the above [1] to [6], wherein the culture is carried out under conditions in which one or more compounds selected from the group consisting of nicotinamide, N-acetylcysteine, a p38 inhibitor and a ROCK inhibitor are further present.

[8] The method according to the above [7], wherein the p38 inhibitor is SB202190, and the ROCK inhibitor is Y-27632.

[9] The method according to any one of the above [1] to [8], wherein the induced pluripotent stem cells are human induced pluripotent stem cells.

[10] A method for preparing intestinal epithelial cell-like cells, which comprises a step of allowing the intestinal stem cell-like cells cultured by the method according to any one of the above [1] to [9] to differentiate into intestinal epithelial cell-like cells.

[11] The intestinal epithelial cell-like cells obtained by the method according to the above [10].

[12] A method for evaluating the pharmacokinetics or toxicity of a test substance, using the intestinal epithelial cell-like cells according to the above [11].

[13] The method according to the above [12], wherein the pharmacokinetics is metabolism, absorption, excretion, drug interaction, induction of a drug-metabolizing enzyme, or induction of a drug transporter.

[14] The method according to the above [12] or [13], comprising the following steps (i) to (iii):
  (i) a step of preparing a cell layer composed of the intestinal epithelial cell-like cells according to the above [11];
  (ii) a step of allowing the cell layer to come into contact with a test substance; and
  (iii) a step of quantifying the test substance that has permeated through the cell layer, and evaluating the test substance in terms of absorbing property or membrane permeability, drug interaction, induction of a drug-metabolizing enzyme, induction of a drug transporter, or toxicity.

[15] The method according to the above [12] or [13], comprising the following steps (I) and (II):
  (I) a step of allowing the intestinal epithelial cell-like cells according to the above [11] to come into contact with a test substance; and
  (II) a step of measuring and/or evaluating the test substance in terms of the metabolism or absorption of the test substance, drug interaction, induction of a drug-metabolizing enzyme, induction of a drug transporter, or toxicity.

[16] A method for evaluating the gastric mucosa-damaging action of a test substance, comprising the following steps (a) and (b):
  (a) a step of allowing the intestinal epithelial cell-like cells according to the above [11] to come into contact with a test substance; and
  (b) a step of detecting the expression of mucin 2 or chromogranin A in the intestinal epithelial cell-like cells and then determining the gastric mucosa-damaging action of the test substance based on the detection results, wherein a reduction in the expression of mucin 2 or chromogranin A is used as an indicator for the test substance having gastric mucosa-damaging action.

[17] A method for evaluating the gastric mucosa-protecting action of a test substance, comprising the following steps (A) and (B):
  (A) a step of allowing the intestinal epithelial cell-like cells according to the above [11] to come into contact with a test substance in the presence of a substance exhibiting gastric mucosa-damaging action; and
  (B) a step of detecting the expression of mucin 2 or chromogranin A in the intestinal epithelial cell-like cells and then determining the gastric mucosa-protecting action of the test substance based on the detection results, wherein suppression of a reduction in the expression of mucin 2 or chromogranin A by the substance is used as an indicator for the test substance having gastric mucosa-protecting action.

[18] A cell preparation comprising the intestinal epithelial cell-like cells according to the above [11].

Con: Control (Intestinal epithelial cells cultured in a medium, to which indomethacin and rebamipide have not been added.)

I50: Intestinal epithelial cells cultured in a medium, to which 50 μM indomethacin has been added.

I200: Intestinal epithelial cells cultured in a medium, to which 200 μM indomethacin has been added.

R50: Intestinal epithelial cells cultured in a medium, to which 50 μM rebamipide has been added.

R100: Intestinal epithelial cells cultured in a medium, to which 100 μM rebamipide has been added.

R200: Intestinal epithelial cells cultured in a medium, to which 200 μM rebamipide has been added.

I200+R50: Intestinal epithelial cells cultured in a medium, to which 200 μM indomethacin and 50 μM rebamipide have been added.

I200+R100: Intestinal epithelial cells cultured in a medium, to which 200 μM indomethacin and 100 μM rebamipide have been added.

I200+R200: Intestinal epithelial cells cultured in a medium, to which 200 μM indomethacin and 200 μM rebamipide have been added.

SI: Commercially available human small intestinal cells.

Caco-2: Human colon cancer-derived cells.

Figure 6:
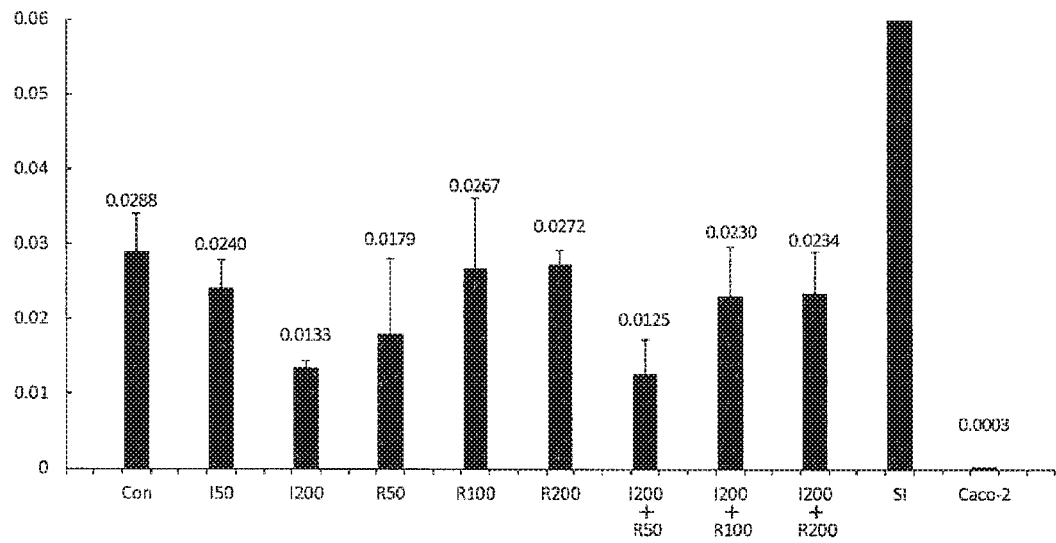

FIG. 6 shows the expression of chromogranin A (CgA) (at an mRNA level) in intestinal epithelial cells that have been differentiated from intestinal stem cells, and the results of an assay using the same. The longitudinal axis indicates a relative value obtained using the expression level of commercially available human small intestinal cells (SI) as a reference (1).

Con: Control (Intestinal epithelial cells cultured in a medium, to which indomethacin and rebamipide have not been added.)

I50: Intestinal epithelial cells cultured in a medium, to which 50 μM indomethacin has been added.

I200: Intestinal epithelial cells cultured in a medium, to which 200 μM indomethacin has been added.

R50: Intestinal epithelial cells cultured in a medium, to which 50 μM rebamipide has been added.

R100: Intestinal epithelial cells cultured in a medium, to which 100 μM rebamipide has been added.

R200: Intestinal epithelial cells cultured in a medium, to which 200 μM rebamipide has been added.

I200+R50: Intestinal epithelial cells cultured in a medium, to which 200 μM indomethacin and 50 μM rebamipide have been added.

I200+R100: Intestinal epithelial cells cultured in a medium, to which 200 μM indomethacin and 100 μM rebamipide have been added.

I200+R200: Intestinal epithelial cells cultured in a medium, to which 200 μM indomethacin and 200 μM rebamipide have been added.

SI: Commercially available human small intestinal cells.

Caco-2: Human colon cancer-derived cells.

Figure 7:
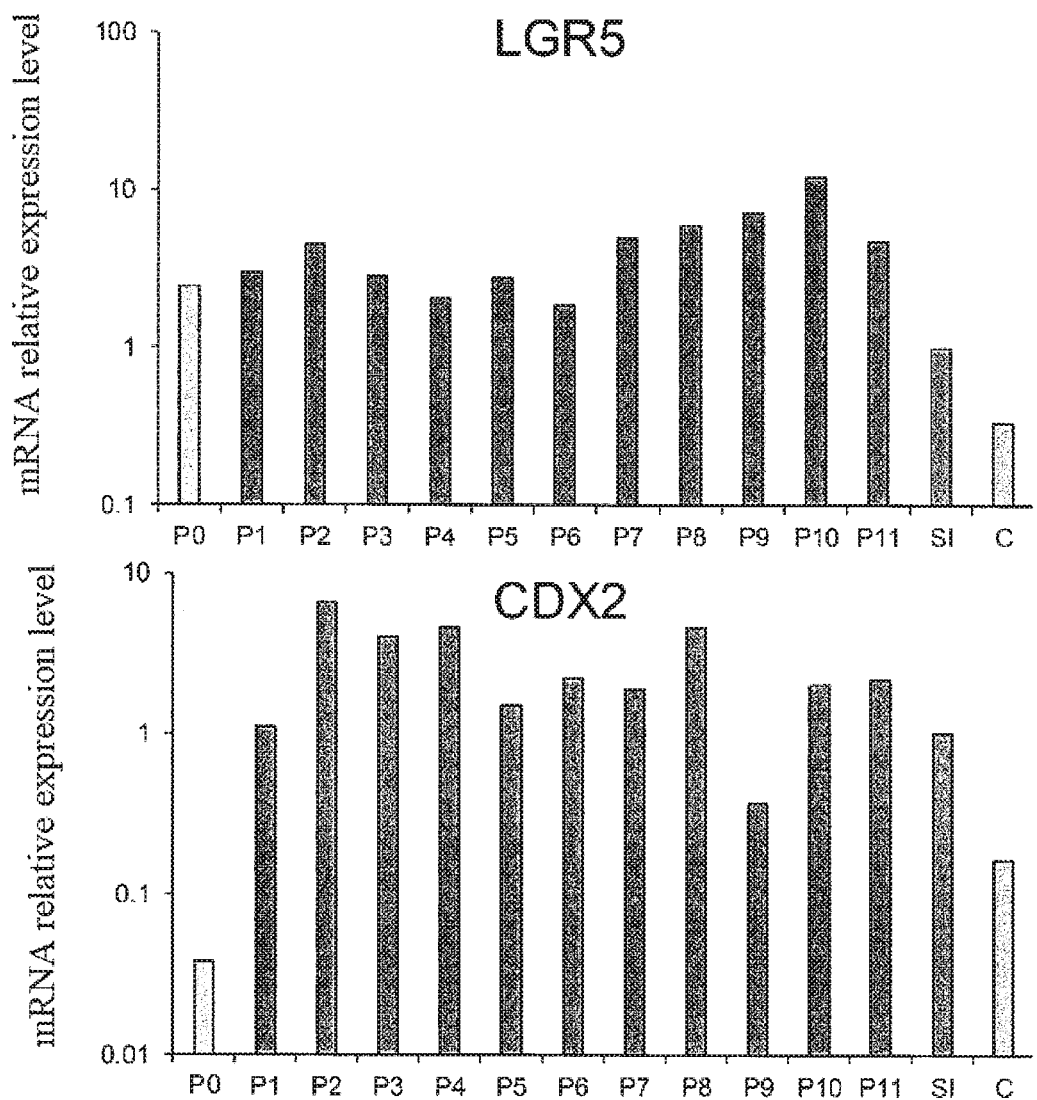

FIG. 7 shows the expression of an intestinal stem cell-related gene in the maintenance culture of intestinal stem cells that have been differentiated from human iPS cells. P0 indicates not-passaged. n=1, P: the number of passages, SI: human small intestine, and C: Caco-2 cells.

Figure 8:
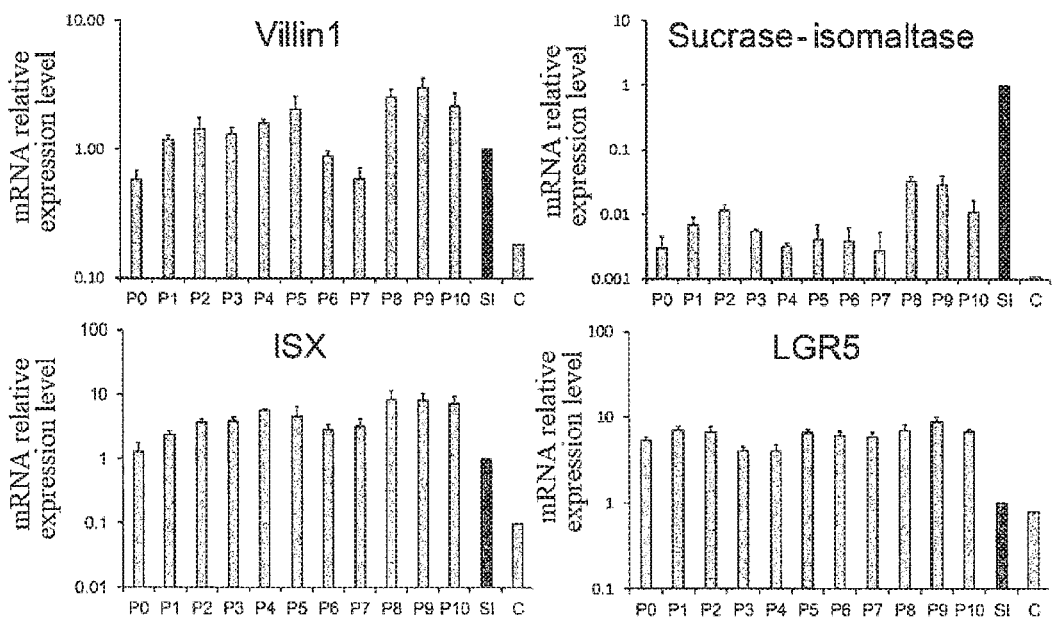

FIG. 8 shows the expression level of mRNA of various types of marker genes in intestinal epithelial cells that have been differentiated from intestinal stem cells. The results are shown as a mean value±S.D. (n=3). P0 indicates a group, in which intestinal stem cells have been differentiated without being subjected to maintenance culture. P: the number of passages, SI: human small intestine, and C: Caco-2 cells.

Figure 9:
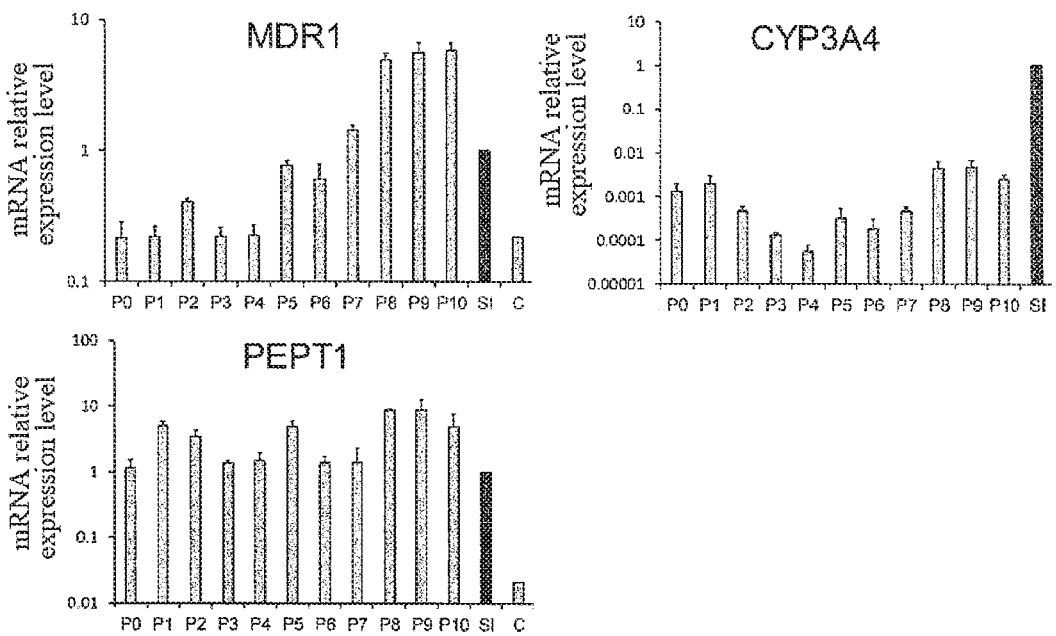

FIG. 9 shows the expression level of mRNA of various types of marker genes in intestinal epithelial cells that have been differentiated from intestinal stem cells. P: the number of passages, SI: human small intestine, and C: Caco-2 cells. Regarding CYP3A4, the expression was not detected in Caco-2 (N.D.).

EMBODIMENT OF CARRYING OUT THE INVENTION

The present invention relates to a method for culturing intestinal stem cell-like cells derived from induced pluripotent stem cells (iPS cells). According to the present invention, it becomes possible to maintain iPS cell-derived intestinal stem cell-like cells and allow them to grow, while maintaining the properties of intestinal stem cells, namely, undifferentiation property, proliferative ability and differentiation ability to differentiate into epithelial cells.

1. Terms

Several terms important in the present invention will be described below. The "iPS cell-derived intestinal stem cell-like cells" are cells exhibiting characteristics similar to intestinal stem cells in a living body, which are obtained by inducing differentiation of iPS cells into an intestinal epithelial cell lineage. If differentiation of the iPS cell-derived intestinal stem cell-like cells is further induced under suitable conditions, cells similar to intestinal epithelial cells in a living body (intestinal epithelial cell-like cells) are obtained. Besides, in the present description, the phrase "to induce differentiation" means that cells are induced to differentiate into a specific cell lineage.

The "induced pluripotent stem cells (iPS cells)" are cells having pluripotency (pluripotent ability) and proliferative ability, which are produced by reprogramming somatic cells by introduction of reprogramming factors, etc. The induced pluripotent stem cells exhibit properties similar to ES cells. The somatic cells used in the production of iPS cells are not particularly limited, and the somatic cells may be either differentiated somatic cells or undifferentiated stem cells. In addition, the origin of the somatic cells is not particularly limited, either, but preferably the somatic cells of mammals (e.g., primates such as humans or chimpanzees, or rodents such as mice or rats), and particularly preferably human somatic cells are used. The iPS cells can be produced by previously reported various types of methods. Also, methods for producing iPS cells, which will be developed in the future, can be naturally applied.

The most basic method for producing iPS cells is a method of introducing four transcriptional factors Oct3/4, Sox2, Klf4 and c-Myc into cells, utilizing virus (Takahashi K, Yamanaka S: Cell 126 (4), 663-676, 2006; Takahashi, K, et al: Cell 131 (5), 861-72, 2007). Regarding human iPS cells, it has been reported that human iPS cells have been established by introduction of four factors Oct4, Sox2, Lin28 and Nonog (Yu J, et al: Science 318 (5858), 1917-1920, 2007). It has also been reported that iPS cells have been established by introduction of the three factors other than c-Myc (Nakagawa M, et al: Nat. Biotechnol. 26 (1), 101-106, 2008), or the two factors Oct3/4 and Klf4 (Kim J B, et al: Nature 454 (7204), 646-650, 2008), or only Oct3/4 (Kim J B, et al: Cell 136 (3), 411-419, 2009). Moreover, a method of introducing a protein as a gene expression product into cells (Zhou H, Wu S, Joo J Y, et al; Cell Stem Cell 4, 381-384, 2009; Kim D, Kim C H, Moon J I, et al: Cell Stem Cell 4, 472-476, 2009) has also been reported. On the other hand, it has been reported that it is possible to improve production efficiency or to reduce factors to be introduced by using BIX-01294 which is an inhibitor against histone methyltransferase G9a, valproic acid (VPA) which is a histone deacetylase inhibitor, BayK8644 or the like (Huangfu D, et al: Nat. Biotechnol. 26 (7), 795-797, 2008; Huangfu D, et al: Nat. Biotechnol. 26 (11), 1269-1275, 2008; Silva J, et al; PLoS. Biol. 6 (10), e 253, 2008). Studies have been conducted also regarding a gene introduction method, and techniques of utilizing the following components other than retrovirus for gene introduction have been developed: rentivirus (Yu J, et al: Science 318 (5858), 1917-1920, 2007), adenovirus (Stadtfeld M, et al: Science 322 (5903), 945-949, 2008), a plasmid (Okita K, et al: Science 322 (5903), 949-953, 2008), a transposon vector (Woltjen K, Michael I P, Mohseni P, et al: Nature 458, 766-770, 2009; Kaji K, Norrby K, Pac a A, et al: Nature 458, 771-775, 2009; Yusa K, Rad R, Takeda J, et al: Nat Methods 6, 363-369, 2009), or an episomal vector (Yu J, Hu K, Smuga-Otto K, Tian S, et al: Science 324, 797-801, 2009).

Transformed iPS cells, namely, iPS cells, in which reprogramming has occurred, can be selected by using, as an indicator, the expression of a pluripotent stem cell marker (undifferentiation marker) such as Fbxo15, Nanog, Oct/4, Fgf-4, Esg-1 and Cript, etc. The selected cells are recovered as iPS cells.

The iPS cells can be provided from National University Corporation, Kyoto University, or National Research and Development Corporation, Riken BioResource Research Center.

2. Culture of Induced Pluripotent Stem Cell-Derived Intestinal Stem Cell-Like Cells One aspect of the culture method of the present invention (which is also referred to as a "first culture method" in the following description) is characterized in that iPS cell-derived intestinal stem cell-like cells obtained by inducing differentiation of iPS cells are cultured in the presence of a GSK-3β inhibitor, a histone deacetylation inhibitor, and a serum replacement. In other words, in the present invention, a step of culturing iPS cell-derived intestinal stem cell-like cells in the presence of a GSK-3β inhibitor, a histone deacetylation inhibitor, and a serum replacement is carried out.

The phrase "in the presence of a GSK-3β inhibitor, a histone deacetylation inhibitor, and a serum replacement" has the same definition as conditions in which these compounds are added into a medium. Accordingly, the cells may be cultured using a medium, into which these compounds have been added. By using these three components in combination, the effect of maintaining the properties of intestinal stem cells, namely, undifferentiation property, proliferative ability and differentiation ability to differentiate the cells into epithelial cells can be expected. Besides, for convenience of explanation, the GSK-3β inhibitor, the histone deacetylation inhibitor, and the serum replacement are collectively referred to as "components of a first group."

In another aspect of the present invention (which is also referred to as a "second culture method" in the following description), among the components of the first group, the histone deacetylation inhibitor is omitted. In other words, the present method is a simplified culture method that is characterized in that the cells are cultured in the presence of a GSK-3β inhibitor and a serum replacement.

Examples of the GSK-3β inhibitor may include CHIR 99021, SB16763, CHIR 98014, TWS119, Tideglusib, SB415286, BIO, AZD2858, AZD1080, AR-A014418, TDZD-8, LY2090314, IM-12, Indirubin, Bikinin, and 1-Azakenpaullone. Likewise, examples of the histone deacetylation inhibitor may include valproic acid, vorinostat, trichostatin A, tubastatin A, givinostat, and pracinostat. On the other hand, the serum replacement is a composition containing differentiation inducing factors, which is used instead of serum in order to culture iPS cells, ES cells, etc., while maintaining the undifferentiated state of the cells. Preferably, a knockout serum replacement (KSR) is used.

The additive concentration of the GSK-3β inhibitor (in the case of CHIR 99021) is, for example, 1 μM to 100 μM, and preferably 3 μM to 30 μM. In the case of the second culture method, 2 μM to 20 μM is also a preferred additive concentration range. Likewise, the additive concentration of the histone deacetylation inhibitor (in the case of valproic acid) is, for example, 0.1 mM to 10 mM, and preferably 0.5 mM to 3 mM, and the additive concentration of the serum replacement (in the case of KSR) is, for example, 5% (v/v) to 20% (v/v), and preferably IV 10% (v/v).

For the reason of preventing a reduction in the activity or growth rate, etc., the medium is exchanged with a fresh one, as necessary. For example, the medium may be exchanged with a fresh one at a frequency of once 24 hours to 3 days. In addition, a subculture may be carried out at a stage in which the cells become confluent or sub-confluent.

In a preferred aspect, the culture is carried out under conditions in which one or more compounds selected from the group consisting of an epidermal growth factor (EGF), a TGFβ receptor inhibitor and a fibroblast growth factor are present in addition to the components of the above-described first group. Besides, for convenience of explanation, the epidermal growth factor (EGF), the TGFβ receptor inhibitor and the fibroblast growth factor are collectively referred to as "components of a second group."

By using the epidermal growth factor, the effect of promoting cell growth can be expected. Likewise, the TGFβ receptor inhibitor can be expected to exhibit the effect of suppressing factors of inducing conversion and differentiation of the cells into mesenchymal cells, and the fibroblast growth factor can be expected to exhibit the effect of promoting cell growth and the effect of suppressing differentiation. Preferably, these components of the second group are all used in combination (together with the components of the first group, a total of 6 components are used in combination).

For example, A-83-01 can be used as a TGFβ receptor inhibitor. In addition, FGF2, FGF4 or FGF10 may be adopted as fibroblast growth factors. These two or three components of the FGF family may be used in combination.

The additive concentration of the epidermal growth factor is, for example, 10 ng/mL to 500 ng/mL, and preferably 50 ng/mL to 200 ng/mL. Likewise, the additive concentration of the TGFβ receptor inhibitor (in the case of A-83-01) is, for example, 0.3 μM to 5 μM, and preferably 0.5 μM to 3 μM, and the additive concentration of the fibroblast growth factor (in the case of FGF2) is, for example, 5 ng/mL to 200 ng/mL, and preferably 20 ng/mL to 50 ng/mL. With regard to the additive concentration of the TGFβ receptor inhibitor in the case of the second culture method, 0.3 µM to 3 µM (in the case of A-83-01) is also a preferred additive concentration range.

In a more preferred aspect, the culture is carried out under conditions in which one or more compounds selected from the group consisting of a BMP inhibitor, a Wnt signaling activator and a Wnt agonist are further present. Besides, for convenience of explanation, the BMP inhibitor, the Wnt signaling activator and the Wnt agonist are collectively referred to as "components of a third group."

By using the BMP inhibitor, the effect of suppressing differentiation of stem cells and maintaining stem cell properties can be expected. Likewise, the Wnt signaling activator can be expected to exhibit the effect of maintaining the growth of stem cells and stem cell properties, and the Wnt agonist can be expected to exhibit the effect of maintaining the growth of stem cells and stem cell properties by activating Wnt signals. Preferably, all of the components of the above-described second group and all of the components of the third group are used in combination (in the case of the first culture method, together with the components of the first group, a total of 9 components are used in combination).

For example, Noggin can be used as a BMP inhibitor. Moreover, for example, R-spondin 1 can be used as a Wnt signaling activator. As a Wnt agonist, for example, Wnt3a can be used.

The additive concentration of the BMP inhibitor (in the case of Noggin) is, for example, 10 ng/mL to 500 ng/mL, and preferably 50 ng/mL, to 200 ng/mL. Likewise, the additive concentration of the Wnt signaling activator (in the case of R-spondin 1) is, for example, 10 ng/mL to 1000 ng/mL, and preferably 50 ng/mL to 500 ng/mL, and the additive concentration of the Wnt agonist (in the case of Wnt3a) is, for example, 10 ng/mL to 500 ng/mL, and preferably 50 ng/mL to 200 ng/mL.

In a further preferred aspect, the culture is carried out under conditions in which one or more compounds selected from the group consisting of nicotinamide, N-acetylcysteine, a p38 inhibitor and a ROCK inhibitor are further present. Besides, for convenience of explanation, nicotinamide, N-acetylcysteine, the p38 inhibitor and the ROCK inhibitor are collectively referred to as "components of a fourth group."

By using nicotinamide, the elect of maintaining stem cell properties can be expected. Likewise, N-acetylcysteine can be expected to exhibit the effect of suppressing cell death, the p38 inhibitor can be expected to exhibit the effect of suppressing cell stress or inflammation and the effect of suppressing differentiation, and the ROCK inhibitor can be expected to exhibit the effect of suppressing cell death. In the first culture method, preferably, all of the components of the above-described second group, all of the components of the above-described third group, and all of these components of the fourth group are used in combination (together with the first group, a total of 13 components are used in combination). In the second culture method, preferably, the components of the third group are omitted, and all of the components of the second group and only the ROCK inhibitor from the components of the fourth group are used in combination (together with the components of the first group (the GSK-3β inhibitor and the serum replacement), a total of 6 components are used in combination).

As a p38 inhibitor, for example, SB202190 can be used. In addition, as a ROCK inhibitor, for example, Y-27632 can be used.

The additive concentration of nicotinamide is, for example, 0.1 mg/mL, to 5 mg/mL, and preferably 0.5 mg/mL to 2 mg/mL. Likewise, the additive concentration of N-acetylcysteine is, for example, 0.1 mM to 5 mM, and preferably 0.5 mM to 2 mM; the additive concentration of the p38 inhibitor (in the case of SB202190) is, for example, 1 µM to 50 mM, and preferably 5 µM to 20 mM; and the additive concentration of the ROCK inhibitor (in the case of Y-27632) is, for example, 1 µM to 50 µM, and preferably 3 µM to 30 µM. Regarding the additive concentration of the ROCK inhibitor in the case of the second culture method, 1 µM to 10 µM (in the ease of Y-27632) is also a preferred additive concentration range. Besides, it is preferred that the ROCK inhibitor is not contained in a culture solution used in medium exchange. However, in the case of the second culture method, conditions in which the ROCK inhibitor is constantly added into the medium may also be adopted.

Regarding other culture conditions (culture temperature, etc.), conditions commonly adopted in the culture of animal cells may be applied. That is to say, the culture may be carried out under the environment of, for example, 37° C. and 5% $CO_2$. In addition, the basic medium is not particularly limited, as long as the maintenance and growth of intestinal stem cell-like cells can be carried out therein. Preferably, a basic medium suitable for the culture of epithelial cells (for example, a mixed medium of D-MEM and Ham's F-12 medium, or D-MEM) is used. Examples of the component that can be added into the medium may include bovine serum albumin (BSA), antibiotics, 2-mercaptoethanol, PVA, non-essential amino acid (NEAA), insulin, transferrin, and selenium. Typically, the cells are two-dimensionally cultured using a culture dish or the like, According to the method of the present invention, intestinal epithelial cell-like cells can be obtained from iPS cells by such a two-dimensional culture. However, a three-dimensional culture may also be carried out using a gel-state culture base material, a three-dimensional culture plate, etc.

Whether or not the cells maintain desired properties during or after the culture can be determined or evaluated by using, as an indicator, the expression of, for example, a leucine rich repeat-containing G protein-conjugated receptor 5 (LGR5) serving as an intestinal stem cell marker, SOX9 serving as an intestinal tract progenitor cell marker, or CDX2 serving as a hindgut marker.

3. Preparation of iPS Cell-Derived Intestinal Stem Cell-Like Cells

A method of preparing iPS cell-derived intestinal stem cell-like cells used in the culture step of the present invention is not particularly limited. For example, iPS cell-derived intestinal stem cell-like cells may be prepared by inducing differentiation of iPS cells according to previous reports. A specific example of the method of preparing iPS cell-derived intestinal stem cell-like cells will be described below. The preparation method of this example comprises a step of allowing iPS cells to differentiate into endoderm-like cells (step (1)) and a step of allowing the obtained endoderm-like cells to differentiate into intestinal stem cell-like cells (step (2)). It is to be noted that the culture conditions applied herein may be conditions commonly adopted in the culture of animal cells, unless otherwise specified. For example, the cells are cultured under the environment of 37° C. and 5% $CO_2$. Moreover, examples of the basic medium that can be used herein include Iscove's Modified Dulbecco's Medium (IMDM) (GIBCO, etc.), Ham's F-12 Medium (HamF12) (SIGMA, Gibco, etc.), Dulbecco's Modified Eagle Medium (D-MEM) (Nacalai Tesque, SIGMA, Gibco, etc.), Glasgow Basic Medium (Gibco, etc.), and RPMI1640 medium. Two or more types of basic media may be used in combination. In the step (2), a basic medium suitable for the culture of epithelial cells (for example, a mixed medium of D-MEM and Ham's F-12 medium, or D-MEM) is preferably used. In addition, examples of the component that can be added into the medium may include bovine serum albumin (BSA), antibiotics, 2-mercaptoethanol, PVA, non-essential amino acid (NEAA), insulin, transferrin, and selenium.

<Step (1) Differentiation into Endoderm-Like Cells>

In this step, iPS cells are cultured, so that the cells are allowed to differentiate into endoderm-like cells. In other words, iPS cells are cultured under condition for inducing differentiation of the iPS cells into endoderm-like cells. The culture conditions are not particularly limited, as long as the iPS cells are able to differentiate into endoderm-like cells. For example, the iPS cells are cultured in a medium, into which activin A is added, according to an ordinary method. In this case, the concentration of activin A in the medium is set at, for example, 10 ng/mL to 200 ng/mL, and preferably 20 ng/mL to 150 ng/mL. From the viewpoint of cell growth rate, maintenance, etc., it is preferable to add serum or a serum replacement (Knockout serum replacement (KSR), etc.) to the medium. The serum is not limited to fetal bovine serum, but human serum, sheep serum, and the like can also be used. The additive amount of serum or a serum replacement is, for example, 0.1% (v/v) to 10% (v/v).

A Wnt/β-catenin signaling pathway inhibitor (e.g., hexachlorophene, quercetin, or Wnt3a as a Wnt ligand) may be added into the medium, so as to promote differentiation of the iPS cells into endoderm-like cells.

In a preferred aspect, two stages of cultures are carded out as a step (1). In a first stage of culture, the culture is carried out in a medium into which a relatively low concentration of serum (e.g., 0.1% (v/v) to 1% (v/v)) is added, and in the subsequent second stage of culture, the culture is carried out in a medium in which the serum concentration is higher than that in the first stage of culture (in which the serum concentration is set at, for example, 1% (v/v) to 10% (v/v)). Thus, adoption of the two stages of cultures is preferable in that the growth of undifferentiated cells is suppressed in the first stage of culture and the differentiated cells are then allowed to grow in the subsequent second stage of culture.

The period of the step (1) (culture period) is, for example, 1 day to 10 days, and preferably 2 days to 7 days. When the two stages of cultures are adopted as a step (1), the period of the first stage of culture is set at, for example, 1 day to 7 days, and preferably 2 days to 5 days, whereas the period of the second stage of culture is set at, for example, 1 day to 6 days, and preferably 1 day to 4 days.

<Step (2) Differentiation into Intestinal Stem Cell-Like Cells>

In this step, the endoderm-like cells obtained in the step (1) are allowed to differentiate into intestinal stem cell-like cells. In other words, endoderm-like cells are cultured under conditions for inducing differentiation the endoderm-like cells into intestinal stem cell-like cells. The culture conditions are not particularly limited, as long as the endoderm-like cells are able to differentiate into intestinal stem cell-like cells. Preferably, the endoderm-like cells are cultured in the presence of FGF2 (fibroblast growth factor 2). Preferably, human FGF2 (e.g., human recombinant FGF2) is used.

Typically, the cell population obtained in the step (1) or a part thereof is subjected to the step (2) without selection. Otherwise, endoderm-like cells may be selected from the cell population obtained in the step (1), and may be then subjected to the step (2). Selection of endoderm-like cells may be carried out, for example, by employing a flow cytometer (cell sorter), using a cell surface marker as an indicator.

The phrase "in the presence of FGF2" has the same definitions as conditions in which FGF2 is added into a medium. Accordingly, in order to perform the culture in the presence of FGF2, the medium into which FGF2 is added may be used. The additive concentration of FGF2 is, for example, 100 ng/mL to 500 mg/mL.

The period of the step (2) (culture period) is, for example, 2 days to 10 days, and preferably 3 days to 7 days. If the culture period is too short, expected effects (an increase in the differentiation efficiency, and promotion of the acquiring of functions as intestinal stem cells) cannot be sufficiently obtained. On the other hand, if the culture period is too long, it causes a reduction in the differentiation efficiency.

Differentiation of the endoderm-like cells into intestinal stem cell-like cells can be determined or evaluated, for example, using the expression of an intestinal stem cell marker as an indicator. Examples of the intestinal stem cell marker may include a leucine rich repeat-containing G protein conjugated receptor 5 (LGR5), and an ephrin B2 receptor (EphB2).

4. Preparation of Intestinal Epithelial Cell-Like Cells

A second aspect of the present invention relates to a method tor preparing intestinal epithelial cell-like cells from the intestinal stem cell-like cells cultured by the culture method of the present invention. The preparation method of the present invention is characterized in that the intestinal stem cell-like cells cultured by the culture method of the present invention are allowed to differentiate into intestinal epithelial cell-like cells. In other words, in the preparation method of the present invention, a step of allowing the intestinal stem cell-like cells cultured by the culture method of the present invention to differentiate into intestinal epithelial cell-like cells (differentiation step) is carried out. The operations, conditions, etc. of the present step are not particularly limited, as long as the intestinal stem cell-like cells can be allowed to differentiate into intestinal epithelial cell-like cells. Specific examples (Example 1 and Example 2) of a preferred differentiation step are shown below. The culture conditions applied in the following Example 1 and Example 2 may be conditions commonly adopted in the culture of animal cells, unless otherwise particularly specified. For example, the cells are cultured under the environment of 37° C. and 5% $CO_2$, and as a basic medium, a basic medium suitable for the culture of epithelial cells (e.g., a mixed medium of D-MEM and Ham's F-12 medium, or D-MEM) is preferably used. In addition, examples of the component that can be added into the medium may include bovine serum albumin (BSA), antibiotics, 2-mercaptoethanol, PVA, non-essential amino acid (NEAA), insulin, transferrin, and selenium.

Differentiation of the intestinal stem cell-like cells into intestinal epithelial cell-like cells can be determined or evaluated, for example, by using, as an indicator, the expression of an intestinal epithelial cell marker or a pharmacokinetics-related gene, incorporation of a peptide, or induction of the expression of a drug-metabolizing enzyme mediated by a vitamin D receptor. Examples of the intestinal epithelial cell marker and the pharmacokinetics-related gene tray include Villin 1, sucrase-isomaltase, SLC (solute carrier) organic anion transporter 2B1 (SLCO2B1/OATP2B1), SLC (solute carrier) family member 15A1/peptide transporter 1 (SLC15A1/PEPT1), SLC (solute carrier) family member 46A1/proton conjugated folate transporter (SLC46A1/PCFT), ATP-binding cassette transporter B1/multidrug resistance protein 1 (ABCB1/MDR1), ATP-binding cassette transporter G2/breast cancer resistance protein (ABCG2/BCRP), caudal homeobox transcriptional factor 2 (CDX2), dipeptidyl peptidase 4 (DPP4), pregnane X receptor (PXR), uridine diphosphate-glucuronosyltransferase 1A1 (UGT1A1), and uridine diphosphate-glucuronosyltransferase 1A4 (UGT1A4). Among these, particularly effective markers are sucrase-isomaltase and Villin 1, which have high specificity to the intestinal tract epithelium, SLC15A1/PEPT1 associated with absorption of a peptide in the small intestine, and SLCO2B1/OATP2B1 associated with absorption of organic anion in the small intestine.

4-1. Example 1 of Differentiation Step

In this example, intestinal stem cell-like cells are cultured in the presence of one or more compounds selected from the group consisting of an MEK1 inhibitor, a DNA methylation inhibitor and a TGFβ receptor inhibitor (hereinafter also referred to as "first inducing) factor(s)") and EGF (hereinafter also referred to as a "second inducing factor"), so that the intestinal stem cell-like cells are allowed to differentiate into intestinal epithelial cell-like cells. Typically, the cell population obtained by applying the culture method of the present invention or a part thereof is subjected to a differentiation step without selection. On the other hand, intestinal stem cell-like cells may be selected from the cell population obtained by applying the culture method of the present invention, and may be then subjected to a differentiation step. Selection of intestinal stem cell-like cells may be carried out, for example, by employing a flow cytometer (cell sorter), using a cell surface marker as an indicator.

The phrase "in the presence of one or more compounds selected from the group consisting of an MEK1 inhibitor, a DNA methylation inhibitor and a TGFβ receptor inhibitor (the first inducing factor(s)) and EGF (the second inducing factor)" has the same definitions as the conditions in which the first inducing factor and the second inducing factor are added into a medium. Accordingly, in order to perform the culture in the presence of the first inducing factor(s) and the second inducing factor, the medium into which the first inducing factor and the second inducing factor are added may be used.

Examples of the MEK1 inhibitor may include PD98059, PD184352, PD184161, PD0325901, U0126, MEK inhibitor I, MEK inhibitor II, MEK1/2 inhibitor II, and SL327. Likewise, examples of the DNA methylation inhibitor may include 5-aza-2'-deoxycytidine, 5-azacitidine, RG108, and zebularine. Regarding the TGFβ receptor inhibitors, if taking into consideration the experimental results in which A-83-01 exhibited inhibitory activity against the TGF-β receptors ALK4, ALK5, and ALK7, the TGFβ receptor inhibitors exhibiting inhibitory activity against one or more of TGF-β receptors ALK4, ALK5, and ALK7 may be preferably used. For example, A-83-01, SB431542, SB-505124, SB525334, D4476, ALK5 inhibitor, LY2157299, LY364947, GW788388, and RepSox satisfy the aforementioned conditions.

The additive concentration of the MEK1 inhibitor (in the case of PD98059) is, for example, 4 µM to 100 µM, and preferably 10 to 40 µM. Likewise, the additive concentration of the methylation inhibitor (in the case of 5-aza-2'-deoxycytidine) is, for example, 1 µM to 25 µM, and preferably 2.5 µM to 10 µM, and the additive concentration of TGFβ receptor inhibitor (in the case of A-83-01) is, for example, 0.1 µM to 2.5 µM, and preferably 0.2 µM to 1 µM.

In a preferred aspect, as first inducing factors, two or more of the MEK1 inhibitor, the DNA methylation inhibitor, and the TGFβ receptor inhibitor are used in combination. By using two or more different first inducing factors in combination, additive or synergistic effects are obtained, and differentiation into the intestinal tract epithelium can be promoted. Most preferably, all (namely, three types of) first inducing factors are used in combination.

The period of the present step (culture period) is, for example, 7 days to 30 days, and preferably 10 days to 20 days. If the culture period is too short, expected effects (an increase in the differentiation efficiency, and promotion of the acquiring of functions as intestinal epithelial cells) cannot be sufficiently obtained. On the other hand, if the culture period is too long, it causes a reduction in the differentiation efficiency.

In a preferred aspect, in the present step, two stages of cultures are carried out, namely, a step of culturing the intestinal stem cell-like cells obtained by applying the culture method of the present invention in the presence of a GSK inhibitor (e.g., GSK3iXV) and/or a BMP inhibitor (e.g., dorsomorphin) and EGF (differentiation step 1), and then, a step of culturing the resulting cells in the presence of one or more compounds selected from the group consisting of an MEK1 inhibitor, a DNA methylation inhibitor and a TGFβ receptor inhibitor (first inducing factor(s)) and EGF (second inducing factor) (differentiation step 2) are carried out. Accordingly, in this aspect, before performing the culture using the first inducing factor(s) and the second inducing factor, the culture is carried out in the presence of a GSK inhibitor and/or a BMP inhibitor. A main purpose of the culture performed in the GSK inhibitor and/or the BMP inhibitor is to promote the growth of intestinal stem cells.

When the differentiation step 1 and the differentiation step 2 are carried out, the culture period of the differentiation step 1 is, for example, 3 days to 14 days, and preferably 4 days to 10 days, whereas the culture period of the differentiation step 2 is, for example, 3 days to 21 days, and preferably 5 days to 15 days.

In each step, a subculture may be carried out in the midcourse of the step. For example, when the cells become confluent or sub-confluent, a part of the cells is harvested, and is then transferred into another culture vessel, and the culture is continued. In order to promote differentiation, the cell density is preferably set at low. For example, the cells may be seeded at a cell density of approximately $1 \times 10^4$ cells/cm$^2$ to $1 \times 10^6$ cells/cm$^2$.

Upon the recovery of the cells attended with medium exchange, subculture, etc., in order to suppress cell death, it may be adequate if the cells have previously been treated with a ROCK inhibitor (Rho-associated coiled-coil forming kinase/Rho-binding kinase) such as Y-27632.

In order to obtain a cell population consisting of only the cells of interest (intestinal epithelial cell-like cells) or a cell population comprising the cells of interest at a high rate (with high purity), a cell population after the culture may be selected and/or fractionated using, as an indicator, a cell surface marker characteristic for the cells of interest.

4-2. Example 2 of Differentiation Step

In this example, the intestinal stem cell-like cells obtained by applying the culture method of the present invention are cultured in the presence of an MEK1 inhibitor, a DNA methylation inhibitor, a TGFβ receptor inhibitor and EGF (hereinafter this condition is referred to as a "first condition") and under conditions in which cAMP is supplied to the cells (hereinafter this condition is referred to as a "second condition"), so that the intestinal stem cell-like cells are allowed to differentiate into intestinal epithelial cell-like cells. Typically, the cell population obtained by applying the culture method of the present invention or a part thereof is subjected to a differentiation step without selection. On the other hand, from a cell population obtained by applying the culture method of the present invention, intestinal stem cell-like cells may be selected, and thereafter, a differentiation step may be carried out on the selected cells. Selection of the intestinal stem cell-like cells may be carried out, for example, by employing a flow cytometer (cell sorter), using a cell surface marker as an indicator.

The first condition, namely, the presence of an MEK1 inhibitor, a DNA methylation inhibitor, a TGFβ receptor inhibitor and EGF has the same definitions as conditions in which these compounds are added into a medium. Accordingly, in order to satisfy the first condition, a medium, into which these compounds are added, may be used.

Examples of the MEK1 inhibitor may include PD98059, PD184352, PD184161, PD0325901, U0126, MEK inhibitor I, MEK inhibitor II, MEK1/2 inhibitor II, and SL327. Likewise, examples of the DNA methylation inhibitor may include 5-aza-2'-deoxycytidine, 5-azacitidine, RG108, and zebularine. Regarding the TGFβ receptor inhibitors, taking into consideration the experimental results that A-83-01 has exhibited inhibitory activity against the TGF-β receptors ALK4, ALK5, and ALK7, the TGFβ receptor inhibitors exhibiting inhibitory activity against one or more of the TGF-β receptors ALK4, ALK5, and ALK7 may be preferably used. For example, A-83-01, SB431542, SB-505124, SB525334, D4476, ALK5 inhibitor, LY2157299, LY364947, GW788388, and RepSox satisfy the aforementioned conditions.

The additive concentration of the MEK1 inhibitor (in the case of PD98059) is, for example, 4 μM to 100 μM, and preferably 10 to 40 μM. Likewise, the additive concentration of the methylation inhibitor (in the case of 5-aza-2'-deoxycytidine) is, for example, 1 μM to 25 μM, and preferably 2.5 μM to 10 μM, whereas the additive concentration of the TGFβ receptor inhibitor (in the case of A-83-01) is, for example, 0.1 μM to 2.5 μM, and preferably 0.2 μM to 1 μM, Besides, with regard to the additive concentration in the case of using a compound different from the exemplified compounds such as PD98059, 5-aza-2'-deoxycytidine and A-83-01, if taking into consideration differences between the properties of a compound to be used and the properties of the exemplified compounds (PD98059, 5-aza-2'-deoxycytidine, and A-83-01) (in particular, a difference in the activity), a person skilled in the art can determine a suitable additive concentration within the above-described concentration range. In addition, whether or not the determined concentration range is appropriate can be confirmed by preliminary experiments.

The second condition, namely, the condition in which cAMP is supplied to the cells has the same definitions as conditions in which a compound, which can be incorporated into the cells and acts as cAMP after it has been incorporated into the cells, is present. Accordingly, in order to satisfy the second condition, for example, a medium, into which a cAMP derivative that can be incorporated into the cells is added, may be used. Examples of the cAMP derivative that can be adopted herein may include PKA activators (e.g., 8-Br-cAMP (8-Bromoadenosine-3',5'-cyclic monophosphate sodium salt, CAS Number: 76939-46-3), 6-Bnz-cAMP (N6-Benzoyladenosine-3',5'-cyclic monophosphate sodium salt, CAS Number: 1135306-29-4), cAMPS-Rp ((R)-Adenosine, cyclic 3',5'-(hydrogenphosphorothioate) triethylammonium salt, CAS Number: 151837-09-1), cAMPS-Sp ((S)-Adenosine, cyclic 3',5'-(hydrogenphosphorothioate) triethylammonium salt, CAS Number: 93602-66-5), Dibutyryl-cAMP (N6,O2'-Dibutyryl adenosine 3',5'-cyclic monophosphate sodium salt, CAS Number: 16980-89-5), and 8-Cl-cAMP (8-Chloroadenosine-3',5'-cyclic monophosphate salt, CAS Number: 124705-03-9)), and Epac activators (Rp-8-Br-cAMPS (8-Bromoadenosine 3',5'-cyclic Monophosphothioate, Rp-Isomer sodium salt, CAS Number: 129735-00-8), 8-CPT-cAMP (8-(4-Chlorophenyl-thio)adenosine 3',5'-cyclic monophosphate, CAS Number: 93882-12-3), 8-pCPT-2'-O-Me-cAMP (8-(4-Chlorophenyl-thio)-2'-O-methyl adenosine 3',5' cyclic monophosphate monosodium, CAS Number: 634207-53-7), etc.). The additive concentration of the cAMP derivative (in the case of 8-Br-cAMP) is, for example, 0.1 mM to 10 mM, preferably 0.2 mM to 5 mM, and more preferably 0.5 mM to 2 mM. Besides, with regard to the additive concentration in the case of using a compound different from the exemplified compound, namely, 8-Br-cAMP, if taking into consideration differences between the properties of a compound to be used and the properties of the exemplified compound (8-Br-cAMP) (in particular, a difference in the activity), a person skilled in the art can determine a suitable additive concentration within the above-described concentration range. In addition, whether or not the determined concentration range is appropriate can be confirmed by preliminary experiments.

The period of the present step (culture period) is, for example, 7 days to 40 days, and preferably 10 days to 30 days. If the culture period is too short, expected effects (an increase in the differentiation efficiency, and promotion of the acquiring of functions as intestinal epithelial cells) cannot be sufficiently obtained. On the other hand, if the culture period is too long, it causes a reduction in the differentiation efficiency.

In order to obtain a cell population consisting of only the cells of interest (intestinal epithelial cell-like cells) or a cell population comprising the cells of interest at a high rate (with high purity), a cell population after the culture may be selected and/or fractionated using, as an indicator, a cell surface marker characteristic for the cells of interest.

Preferably, as a differentiation step, any one of the following culture steps A to C is carried out.
<Culture Step A>

In the culture step A, the following cultures are carried out: a culture (a-1) performed in the presence of an MEK1 inhibitor, a DNA methylation inhibitor, a TGFβ receptor inhibitor and EGF; and then, following the culture (a-1), a culture (a-2) performed in the presence of an MEK1 inhibitor, a DNA methylation inhibitor, a TGFβ receptor inhibitor and EGF, and under conditions in which cAMP is supplied to the cells. Specifically, two stages of cultures, which are different from each other in terms of the presence or absence of conditions in which cAMP is supplied to the cells, are carried out. By doing so, effects such as promotion of differentiation into intestinal epithelial cells, maturation, and the acquiring of functions can be obtained. The period of the culture (a-1) is, for example, 1 day to 5 days. Likewise, the period of the culture (a-2) is, for example, 3 days to 15 days. It is to be noted that the above-described corresponding explanations are applied to matters that are not particularly explained (compounds usable in each culture, the additive concentration of each compound, etc.).

The culture (a-2) may also be carried out under conditions in which a cAMP-decomposing enzyme inhibitor is present, in addition to the MEK1 inhibitor, the DNA methylation inhibitor, the TGFβ receptor inhibitor and EGF. By adopting these conditions, a decrease in the intracellular cAMP concentration is suppressed by inhibition of the decomposition of cAMP, and as a result, induction of differentiation into the intestinal tract epithelium, and in particular, promotion of the acquiring of the functions as intestinal epithelial cells can be expected. That is to say, the aforementioned conditions are advantageous for preparation of more functional intestinal epithelial cell-like cells. Examples of the cAMP-decomposing enzyme inhibitor may include IBMX (3-isobutyl-1-methylxanthine) (MIX), Theophylline, Papaverine, Pentoxifylline (Trental), KS-505, 8-Methoxymethyl-IBMX, Vinpocetine (TCV-3B), EHNA, Trequinsin (HL-725), Lixazinone (RS-82856), (IN-186126), Cilostamide (OPC3689), Bemoradan (RWJ-22867), Anergrelide (BL4162A), Indolidan (LY195115), Cilostazol (OPC-13013), Milrinone (WIN47203), Siguazodan (SKF-94836), 5-Methyl-imazodan (Cl 930), SKF-95654, Pirilobendan (UD-CG 115 BS), Enoximone (MDL 17043), Imazodan (CL 914), SKF-94120, Vesnarinone (OPC 8212), Rolipram (Ro-20-1724), (ZK-62711), Denbufyll'ine, Zaprinast (M&B-22, 948), Dipyridamole, Zaprinast (M&B-22, 948), Dipyridamole, Zardaverine, AH-21-132, and Sulmazol (AR-L 115 BS). The additive concentration of the CAMP-decomposing enzyme inhibitor (in the case of IBMX) is, for example, 0.05 mM to 5 mM, preferably 0.1 mM to 3 mM, and more preferably 0.2 mM to 1 mM. Besides, with regard to the additive concentration in the case of using a compound different from the exemplified compound, namely; IBMX, if taking into consideration differences between the properties of a compound to be used and the properties of the exemplified compound (IBMX) (in particular, a difference in the activity), a person skilled in the art can determine a suitable additive concentration within the above-described concentration range. In addition, whether or not the determined concentration range is appropriate can be confirmed by preliminary experiments.

After completion of the culture (a-2), a culture may also be carried out in the presence of an MEK1 inhibitor, a DNA methylation inhibitor, a TGFβ receptor inhibitor and EGF (culture (a-3)). The period of this culture is, for example, 1 day to 10 days. If this culture is carried out, effects such as promotion of differentiation into intestinal epithelial cells, maturation, and the acquiring of functions can be obtained.

<Culture Step B>

In the culture step B, the following cultures are carried out: a culture (b-1) performed in the presence of an MEK1 inhibitor, a DNA methylation inhibitor, a TGFβ receptor inhibitor and EGF, and under conditions in which cAMP is supplied to the cells; and then, following the culture (b-1), a culture (b-2) performed in the presence of an MEK1 inhibitor, a DNA methylation inhibitor, a TGFβ receptor inhibitor, EGF and a cAMP-decomposing enzyme inhibitor. Thus, if cells are cultured under conditions in which a cAMP-decomposing enzyme inhibitor is present, after the cells have been cultured under conditions in which cAMP has been applied to the cells, effects such as promotion of differentiation into intestinal epithelial cells, maturation, and the acquiring of functions can be obtained. The period of the culture (b-1) is, for example, 3 days to 15 days. Likewise, the period of the culture (b-2) is, for example, 3 days to 15 days. It is to be noted that the above-described corresponding explanations are applied to matters that are not particularly explained (compounds usable in each culture, the additive concentration of each compound, etc.).

The culture (b-1) may also be carried out under conditions in which a cAMP-decomposing enzyme inhibitor is also present, in addition to the MEK1 inhibitor, the DNA methylation inhibitor, the TGFβ receptor inhibitor and EGF. By adopting these conditions, a decrease in the in the intracellular cAMP concentration is suppressed from the early stage, and as a result, induction of differentiation into the intestinal tract epithelium, and in particular, promotion of the acquiring of the functions as intestinal epithelial cells can be expected. That is to say, the aforementioned conditions are advantageous for efficient preparation of more functional intestinal epithelial cell-like cells.

After completion of the culture (b-2), a culture may also be carried out in the presence of an MEK1 inhibitor, a DNA methylation inhibitor, a TGFβ receptor inhibitor and EGF (culture (b-3)). The period of this culture is, for example, 1 day to 10 days. If this culture is carried out, effects such as promotion of differentiation into intestinal epithelial cells, maturation, and the acquiring of functions can be obtained.

<Culture Step C>

In the culture step C, a culture (c-1) is carried out in the presence of an MEK1 inhibitor, a DNA methylation inhibitor, a TGFβ receptor inhibitor and EGF, and under conditions in which cAMP is supplied to the cells. The period of the culture (c-1) is, for example, 3 days to 15 days. It is to be noted that the above-described corresponding explanations are applied to matters that are not particularly explained (compounds usable in each culture, the additive concentration of each compound, etc.).

The culture (c-1) may also be carried out under conditions in which a cAMP-decomposing enzyme inhibitor is also present, in addition to the MEK1 inhibitor, the DNA methylation inhibitor, the TGFβ receptor inhibitor and EGF (wherein conditions in which cAMP is supplied to the cells are also used in combination). By adopting these conditions, a decrease in the intracellular cAMP concentration is suppressed, while supplying cAMP to the cells. Accordingly, the conditions become effective for maintaining intracellular cAMP at a high level, and as a result, it can be expected to promote efficient induction of differentiation into intestinal epithelial cells.

After completion of the culture (c-1), a culture may also be carried out in the presence of an MEK1 inhibitor, a DNA methylation inhibitor, a TGFβ receptor inhibitor and EGF (culture (c-2)). The period of this culture is, for example, 1 day to 10 days. If this culture is carried out, effects such as promotion of differentiation into intestinal epithelial cells, maturation, and the acquiring of functions can be obtained.

In each step constituting the present invention, a subculture may also be carried out in the midcourse of the step. For example, when the cells have become confluent or subconfluent, a portion of the cells is harvested, and is then transferred into another culture vessel, and the culture is continued. In order to promote differentiation, the cell density is preferably set at low. For example, the cells may be seeded at a cell density of approximately $1 \times 10^4$ cells/cm$^2$ to $1 \times 10^6$ cells/cm$^2$.

Upon the recovery of the cells attended with medium exchange, subculture, etc., in order to suppress cell death, it may be adequate if the cells have previously been treated with a ROCK inhibitor (Rho-associated coiled-coil forming kinase/Rho-binding kinase) such as Y-27632.

5. Intended Use of Intestinal Epithelial Cell-Like Cells

A further aspect of the present invention relates to intended use of intestinal epithelial cell-like cells. As a first intended use, various types of assays are provided. The intestinal epithelial cell-like cells of the present invention can be used in an intestinal tract model system, in particular, in a small intestine model system, and the present intestinal epithelial cell-like cells are useful for evaluation of pharmacokinetics absorption, metabolism, etc.) or toxicity in the intestinal tract, in particular, in the small intestine. In other words, the intestinal epithelial cell-like cells of the present invention are utilized in evaluation of the pharmacokinetics or toxicity of compounds.

Specifically, using the intestinal epithelial cell-like cells of the present invention, a test substance can be examined in terms of absorbing property or membrane permeability, drug interaction, induction of a drug-metabolizing enzyme, induction of a drug transporter, toxicity, etc. That is to say, as one intended use of the intestinal epithelial cell-like cells, the present invention provides a method for evaluating a test substance in terms of absorbing property or membrane permeability, drug interaction, induction of a drug-metabolizing enzyme, induction of a drug transporter, toxicity, etc. (a first aspect). In the present method, the following steps are carried out: (i) a step of preparing a cell layer composed of the intestinal epithelial cell-like cells obtained by the differentiation induction method of the present invention; (ii) a step of allowing the cell layer to come into contact with a test substance; and (iii) a step of quantifying the test substance that has permeated through the cell layer, and evaluating the test substance in terms of absorbing property or membrane permeability, drug interaction, induction of a drug-metabolizing enzyme, induction of a drug transporter, or toxicity. It is to be noted that the absorbing property of the test substance can also be evaluated by the after-mentioned method (a second aspect).

In the step (i), typically, the intestinal epithelial cell-like cells are cultured on a semipermeable membrane (porous membrane) to form a cell layer. Specifically, for example, a culture vessel equipped with a culture insert (e.g., Transwell (registered trademark) provided by Corning) is used to seed the cells in the culture insert and then to culture them, so as to obtain a cell layer constituted with the intestinal epithelial cell-like cells.

In the step (ii), the "contact" is typically carried out by adding a test substance into a medium. The timing of adding the test substance is not particularly limited. Accordingly, after a culture has been initiated in a medium not containing a test substance, the test substance may be added at a certain time point, or a culture may be initiated in a medium previously containing a test substance.

As test substances, organic compounds or inorganic compounds having various sizes can be used. Examples of the organic compounds may include nucleic acids, peptides, proteins, lipids (simple lipids, complex lipids (phosphoglyceride, sphingolipid, glycosyl glyceride, cerebroside, etc.), prostaglandin, isoprenoid, terpene, steroid, polyphenol, catechin, and vitamin (B1, B2, B3, B5, B6, B7, B9, B12, C, A, D, E, etc.). Some preferred examples of the test substances may include the existing components such as pharmaceutical products, nutritional food products, food additives, agrichemicals, and perfumes and cosmetics (cosmetic products), and candidate components thereof. Plant extracts, cell extracts, culture supernatants and the like may also be used as test substances. By adding two or more types of test substances simultaneously, the interaction, synergic action and the like between the test substances may also be examined. The test substance may be either a naturally-derived test substance or a synthesized test substance. In the latter case, an efficient assay system can be constructed, for example, by utilizing a combinatorial synthetic method.

The period in which the test substance is allowed to come into contact with the cell layer can be arbitrarily set. The contact period is, for example, 10 minutes to 3 days, and preferably 1 hour to 1 day. The contact may be carried out dividedly over several times.

In the step (iii), the test substance that has permeated through the cell layer is quantified. For example, in the case of using a culture vessel equipped with a culture insert such as Transwell (registered trademark), the test substance that has permeated through the culture insert, that is, the test substance that has moved to the upper portion or lower portion in the vessel through the cell layer is quantified by a measurement method such as mass spectrometry, liquid chromatography, and immunological methods (e.g., fluorescence immunoassay (FIA method) or enzyme immunoassay (EIA method)), depending on the type of the test substance. Based on the quantification results (the amount of the test substance permeating through the cell layer) and the amount of the test substance used (typically, the amount of the test substance added into the medium), the test substance is determined and/or evaluated, in terms of absorbing property or membrane permeability, drug interaction, induction of a drug-metabolizing enzyme, induction of a drug transporter, or toxicity.

As another aspect (a second aspect), the present invention provides a method for evaluating the metabolism or absorption of a test substance. In the present method, the following steps are carried out: (I) a step of allowing the intestinal epithelial cell-like cells obtained by the differentiation induction method of the present invention to come into contact with a test substance; and (II) a step of measuring and/or evaluating the test substance, in terms of metabolism or absorption, drug interaction, induction of a drug-metabolizing enzyme, induction of a drug transporter, or toxicity.

The step (I), namely, the contact of the intestinal epithelial cell-like cells with the test substance can be carried out in the same manner as that of the above-described step (ii). However, it is not essential to previously form a cell layer.

After completion of the step (I), the test substance is measured and/or evaluated, in terms of metabolism or absorption, drug interaction, induction of a drug-metabolizing enzyme, induction of a drug transporter, or toxicity (step (II)). Immediately after completion of the step (I), namely, after completion of the contact with the test substance, the metabolism and the like may be measured and/or evaluated without having substantial time intervals. Otherwise, the metabolism and the like may also be measured and/or evaluated after a certain period of time (e.g., 10 minutes to 5 hours) has passed. The metabolism can be measured, for example, by detecting a metabolite. In this case, in general, the culture solution obtained after completion of the step (I) is used as a sample, and a predicted metabolite is qualitatively or quantitatively measured. A suitable measurement method may be selected depending on the type of the metabolite, and for example, mass spectrometry; liquid chromatography, immunological methods (e.g., fluorescence immunoassay (FIA method) or enzyme immunoassay (EIA method)), and the like can be adopted.

Typically, when a metabolite of the test substance is detected, it is determined or evaluated that "the test substance has been metabolized." Moreover, depending on the amount of the metabolite, the amount of the test substance metabolized can be evaluated. Based on the detection results of the metabolite and the amount of the test substance used (typically, the amount of the test substance added into the medium), the metabolic efficiency of the test substance may be calculated.

It is also possible to measure the metabolism of the test substance, using the expression of a drug-metabolizing enzyme (cytochrome P450 (in particular, CYP3A4), uridine diphosphate-glucuronosyltransferase (in particular, UGT1A8 and UGT1A10), sulfotransferase (in particular, SULT1A3, etc.)) in the intestinal epithelial cell-like cells, as an indicator. The expression of such a drug-metabolizing enzyme can be evaluated at the level of mRNA or a protein. For example, when an increase in the mRNA level of the drug-metabolizing, enzyme has been observed, it can be determined that "the test substance has been metabolized." Likewise, when an increase in the activity of the drug-metabolizing enzyme has been observed, it can be determined that "the test substance has been metabolized." As in the case of making determination using a metabolite as an indicator, determination and/or evaluation may be quantitatively carried out, based on the expression level of the drug-metabolizing enzyme.

In order to evaluate absorption of the test substance, for example, the amount of the test substance remaining in the culture solution is measured. In general, the culture solution obtained after completion of the step (I) is used as a sample, and the test substance is quantified. An appropriate measurement method may be selected depending on the type of the test substance. Examples of the measurement method that can be adopted herein may include mass spectrometry, liquid chromatography, and immunological methods (e.g., fluorescence immunoassay (FIA method) or enzyme immunoassay (EIA method)). Typically, when a decrease in the content of the test substance in the culture solution is observed, it is determined and/or evaluated that "the test substance has been absorbed." In addition, it can also be possible to determine and/or evaluate the amount of the test substance absorbed or absorption efficiency based on the degree of the decrease in the content of the test substance. Besides, absorption can also be evaluated by measuring the amount of the test substance incorporated into the cells.

It is to be noted that the measurement and/or evaluation of metabolism may be carried out at the same time as, or in parallel with the measurement and/or evaluation of absorption.

As described in the Examples later, it has been elucidated that mucin 2 and chromogranin A (CgA), which are highly expressed in human small intestinal epithelial cells, are expressed at a significantly high level in the induced pluripotent stem cell-derived intestinal epithelial cell-like cells, which are prepared utilizing the method of the present invention, and that the expression level of mucin 2 and chromogranin. A (CgA) in the iPS cell-derived intestinal epithelial cell-like cells is incomparably higher than in Caco-2 cells (human colon cancer-derived cells) that are frequently used as a small intestine model system. This fact proves that the present induced pluripotent stem cell-derived intestinal epithelial cell-like cells are extremely highly valuable as a small intestine model system, and at the same time, demonstrates that the expression of mucin 2 and CgA is useful as an indicator for an assay using the present cells. Hence, the present invention provides, as a further aspect of an assay using the intestinal epithelial cell-like cells (third aspect), two evaluation methods using the expression of mucin 2 or CgA as an indicator, namely, a method for evaluating the gastric mucosa-damaging action of the test substance (a third aspect; hereinafter also abbreviated as an "damaging action evaluation method") and a method for evaluating the gastric mucosa-protecting action of the test substance (a fourth aspect; hereinafter also abbreviated as an "protecting action evaluation method"). The damaging action evaluation method of the present invention is particularly useful for prediction of a drug that is likely to cause, as a side effect, mucous membrane disorder (ulcer) (prediction of the risk of causing side effects), whereas the protecting action evaluation method of the present invention is particularly useful for screening for a novel drug having action to suppress such side effects or stress ulcer.

In the damaging action evaluation method of the present invention (third aspect), the following steps are carried out: (a) a step of allowing the intestinal epithelial cell-like cells obtained by the differentiation induction method of the present invention to come into contact with a test substance; and (b) a step of detecting the expression of mucin 2 or CgA in the intestinal epithelial cell-like cells and then determining the gastric mucosa-damaging action of the test substance based on the detection results, wherein a reduction in the expression of mucin 2 or CgA is used as an indicator for the test substance having gastric mucosa-damaging action.

The step (a), namely, the contact of the intestinal epithelial cell-like cells with the test substance can be carried out in the same manner as that of the above-described aspects (first aspect and second aspect). However, it is not essential to previously form a cell layer. Since the usable test substance is also the same as that in the above-described aspects (first aspect and second aspect), the explanation thereof is omitted herein In the step (b) following the step (a), the expression of mucin 2 or CgA is detected in the intestinal epithelial cell-like cells, and based on the detection results, the gastric mucosa-damaging action of the test substance is determined. Specifically, in the present invention, utilizing the expression of mucin 2 or CgA, the gastric mucosa-damaging action of the test substance is determined. More specifically, a decrease in the expression of mucin 2 or CgA is used as an indicator for that the test substance has gastric mucosa-damaging action. Accordingly, when a decrease in the expression of mucin 2 or CgA is found, the test substance is determined to have gastric mucosa-damaging action, and when a decrease in the expression of mucin 2 or CgA is not found, the test substance is determined not to have gastric mucosa-damaging action. Based on the degree (level) of such a decrease in the expression of mucin 2 or CgA, the strength (degree) of the gastric mucosa-damaging action may be determined. Moreover, when a plurality of test substances are used, based on the degree (level) of a decrease in the expression of mucin 2 or CgA, the test substances may be compared with one another in terms of the degree of the gastric mucosa-damaging action and may be evaluated.

Both mucin 2 and CgA are secretory proteins. Mucin 2 is a mucosal material associated with protection of the mucosal membrane of the intestinal tract, and it has been known that a reduction in the quality or amount of mucin 2 induces ulcerative colitis or cancer. On the other hand, CgA is a substance secreted as a result of stimulation of the autonomic nerve, and the blood concentration of CgA has been clinical-chemically known as a tumor marker. In addition, in recent years, the CgA concentration in saliva has been focused as an indicator of stress (Toyota Central R & D Labs., Inc., R & D Review Vol. 34 No. 3, 17-22 (1999, 9), Magazine of Kochi Women's University Academy of Nursing, VOL. 40, NO, 1, pp. 24-30, 2014, etc.).

The expression of mucin 2 and CgA may be detected, for example, according to an ordinary method. Examples of the method of detecting mucin 2 and CgA may include an RT-PCR method, a real-time PCR method (measurement/quantification of mRNA), immunological methods such as fluorescence immunoassay (FIA method) or enzyme immunoassay (EIA method), and mass spectrometry. Regarding detection of CgA, there is a detection reagent or kit (e.g., YK070 Human Chromogranin A provided by Yanaihara Institute Inc.), and these can be utilized.

In general, for comparison, intestinal epithelial cell-like cells, which are not allowed to conic into contact with a test substance (wherein other conditions are identical) (hereinafter referred to as a "control"), are prepared, and the expression of mucin 2 or CgA in such a control is also detected. Then, by comparing the expression level of mucin 2 or CgA in the cells allowed to come into contact with the test substance with the expression level of mucin 2 or CgA in the control, whether the test substance has decreased the expression of mucin 2 or CgA is determined. Thus, by determining the gastric mucosa-damaging action of the test substance based on the comparison with the control, highly reliable determination results can be obtained.

In the protecting action evaluation method of the present invention (fourth aspect), the following steps are carried out: (A) a step of allowing the intestinal epithelial cell-like cells obtained by the differentiation induction method of the present invention to come into contact with a test substance in the presence of a substance exhibiting gastric mucosa-damaging action; and (B) a step of detecting the expression of mucin 2 or CgA in the intestinal epithelial cell-like cells and then determining the gastric mucosa-protecting action of the test substance based on the detection results, wherein suppression of a reduction in the expression of mucin 2 or CgA by the aforementioned substance is used as an indicator for the test substance having gastric mucosa-protecting action.

In the step (A), in the presence of a substance exhibiting gastric mucosa-damaging action (hereinafter referred to as a "mucous membrane damaging agent"), the intestinal epithelial cell-like cells are allowed to come into contact with a test substance. The contact of the intestinal epithelial cell-like cells with the test substance can be carried out in the same manner as that of the above-described aspect (third aspect), and typically, the intestinal epithelial cell-like cells are cultured in the presence of the mucous membrane damaging agent and the test substance (i.e., a state in which these components are added into a medium). The timing of adding the mucous membrane damaging agent and the test substance into the medium is not particularly limited. Accordingly, for example, the culture of the cells may be initiated in a medium that does not contain the mucous membrane damaging agent and the test substance, and then, at a certain time point, the mucous membrane damaging agent and the test substance may be added into the medium. Alternatively, the culture may be initiated in a medium previously containing the mucous membrane damaging agent and the test substance. The order of adding the mucous membrane damaging agent and the test substance is not particularly limited. That is to say, the former may be first added into the medium, or the latter may be first added thereto. Otherwise, the two components may be simultaneously added into the medium.

Various types of substances, which decrease the expression of mucin 2 and/or CgA and thereby damage the gastric mucosa, can be adopted as mucous membrane damaging agent in the present invention. Examples of the substance that can be used as a mucous membrane damaging agent may include indomethacin, aspirin, ketoprofen, and ibuprofen. The amount of the mucous membrane damaging agent used (additive concentration) may be determined with reference to previous reports regarding the action of the used mucous membrane damaging agent, etc., or through preliminary experiments. Also, two or more substances may be used in combination. Besides, since the test substances that can be used herein are the same as those in the above-described aspects (first aspect and second aspect), the explanation thereof is omitted herein.

In the step (B) following the step (A), the expression of mucin 2 or CgA is detected in the intestinal epithelial cell-like cells, and based on the detection results, the gastric mucosa-protecting action of the test substance is determined. Specifically, in the present invention, utilizing the expression of mucin 2 or CgA, the gastric mucosa-protecting action of the test substance is determined. More specifically, suppression of a decrease in the expression of mucin 2 or CgA due to the mucous membrane damaging agent is used as an indicator for that the test substance has gastric mucosa-protecting action. Accordingly, when the test substance suppresses a decrease in the expression of mucin 2 or CgA by the mucous membrane damaging agent, the test substance is determined to have gastric mucosa-protecting action. On the other hand, when the test substance does not suppress a decrease in the expression of mucin 2 or CgA by the mucous membrane damaging agent, the test substance is determined not to have gastric mucosa-protecting action. Based on the degree (level) of suppression of a decrease in the expression of mucin 2 or CgA, the strength (degree) of the gastric mucosa-protecting action may be determined. Moreover, when a plurality of test substances are used, based on the degree (level) of suppression of a decrease in the expression of mucin 2 or CgA, the individual test substances may be compared with one another in terms of the degree of the gastric mucosa-protecting action, and may be evaluated.

As with the above-described aspect (third aspect), in order to obtain highly reliable determination results, a comparison (control) is established, and the gastric mucosa-protecting action of the test substance is preferably determined by comparison with the control. As a control in this case, the intestinal epithelial cell-like cells that are contacted with the test substance in the absence of the mucous membrane damaging agent, and/or the intestinal epithelial cell-like cells that are not allowed to come into contact with the test substance (wherein the mucous membrane damaging agent is present), can be used.

As mentioned above, the evaluation method of the present aspect (fourth aspect) is particularly useful for screening for a novel drug having an action to suppress mucous membrane disorder occurring as a side effect of a drug, or stress ulcer. When the evaluation method of the present invention is used in screening, an effective test substance is selected based on the determination results obtained in the step (B). When the selected substance has sufficient drug effects, the substance can be directly used as an active ingredient of an intestinal tract mucosa protective agent. On the other hand, when the selected substance does not have sufficient drug effects, modification such as chemical modification is performed on the substance to enhance the drug effects thereof, and thereafter, the substance can be used as an active ingredient of an intestinal tract mucosa protective agent. Of course, even in a case where the substance has sufficient drug effects, similar modification may be performed on the substance for the purpose of further increasing the drug effects.

As a second intended use of the intestinal epithelial cell-like cells prepared by the differentiation induction method of the present invention, a cell preparation comprising the intestinal epithelial cell-like cells is provided. The cell preparation of the present invention can be applied to the treatment of various types of intestinal diseases. In particular, it is considered that the present cell preparation is utilized as a material for regeneration and/or reconstruction of injured intestinal epithelial tissues (including dysfunction). That is to say, it can be expected that the cell preparation will contribute to regenerative medicine. The cell preparation of the present invention can be prepared, for example, by suspending the intestinal epithelial cell-like cells obtained by the method of the present invention in a normal saline, a buffer solution (e.g., a phosphate buffer solution), etc., or by producing a three-dimensional tissue body (an organoid or a spheroid) using the intestinal epithelial cell-like cells. As a single dose, for example, $1 \times 10^5$ to $1 \times 10^{10}$ cells may be contained in the cell preparation. The content of the cells can be adjusted, as appropriate, while taking into consideration use purpose, target disease, the sex, age, and body weight of an applied target (recipient), the condition of the affected area, the condition of the cells, and the like.

For the purpose of protecting the cells, dimethyl sulfoxide (DMSO), serum albumin and the like may be contained in the cell preparation of the present invention, and for the purpose of preventing the mixing of bacteria, antibiotics and the like may be contained therein. Further, for the purpose of the activation, growth or induction of differentiation of the cells, various types of components (vitamins, cytokines, growth factors, steroid, etc.) may be contained therein. Furthermore, the cell preparation of the present invention may also contain pharmaceutically acceptable other components (e.g., a carrier, an excipient, a disintegrator, a buffer, an emulsifier, a suspending agent, a soothing agent, a stabilizer, a preservative, an antiseptic, a nominal saline, etc.).

EXAMPLES

A. Development of Novel Culture Method of Human iPS Cell-Derived Intestinal Stem Cell-Like Cells Aiming for establishing a culture method capable of maintaining and/or proliferating human iPS cell-derived intestinal stem cell-like cells, while maintaining the properties of intestinal stem cells, the following studies have been conducted.

1. Method (1) Cells

Human iPS cells (iPS-51: Windy) were prepared by introducing octamer binding protein 3/4 (OCT3/4), sex determining region Y-box 2 (SOX2), kruppel-like factor 4 (KLF4), and v-myc myelocytomatosis viral oncogene homolog (avian) (c-MYC) into the human fetal lung fibroblasts MRC-5, using a pantropic retrovirus vector, and then cloning human ES cell-like colonies. Such human IPS cells were provided from Dr. Akihiro UMEZAWA, National Center for Child Health and Development. As feeder cells, mouse embryonic fibroblasts (MEF) were used.

(2) Medium

For the culture of MEF, there was used Dulbecco's Modified Eagle Medium (DMEM) supplemented with a 10% fetal bovine serum (FBS), 2 mmol/L L-glutamine (L-Glu), 1% non-essential amino acid (NEAA), 100 units/mL penicillin G, and 100 µg/mL streptomycin. As a stripping solution of MEF, 0.05% trypsin-ethylenediaminetetraacetic acid (EDTA) was used, and as a preservative solution of MEF, CELLBANKER 1 was used. For the maintenance culture of human iPS cells, DMEM Ham's F-12 (DMEM/F12) supplemented with 20% knockout serum replacement (KSR), 0.8% NEAA, 2 mmol/L L-Glu 0.1 mmol/L 2-mercaptoethanol (2-MeE), and 5 ng/mL fibroblast growth factor (FGF) 2 was used. As a stripping solution of human iPS cells, Dulbecco's phosphate buffered saline (PBS) supplemented with 1 mg/mL collagenase IV, 0.25% trypsin, 20% KSR, and 1 mmol/L calcium chloride was used. As a preservative solution of human iPS cells, a cryopreservation solution for use in primate ES/iPS cells was used.

(3) Culture of Human iPS Cells

Human iPS cells were seeded on MEF ($5 \times 10^5$ cells/100 mm dish) treated with Mitomycin C, and were then cultured under conditions of 5% $CO_2$/95% air, in a $CO_2$ incubator at 37° C. The subculture of human iPS cells was carried out at a split ratio of 1:2 to 1:3, after the cells had been cultured for 3 to 5 days. Forty-eight hours after the thawing of the human iPS cells, the medium was exchanged with a fresh one, and thereafter, the medium was exchanged with a fresh one every day.

(4) Differentiation of Human iPS Cells into Intestinal Stem Cells

Differentiation of the human iPS cells into intestinal stem cells was initiated, when the percentage of undifferentiated colonies of human iPS cells became approximately 70% with respect to the culture dish. The human iPS cells were cultured in Roswell Park Memorial Institute (RPMI)+GlutaMAX medium supplemented with 0.5% FBS, 100 ng/mL activin A, 100 units/mL penicillin G, and 100 µg/mL streptomycin for 2 days, and thereafter, were cultured in RPMI+GlutaMAX medium supplemented with 2% FBS, 100 ng/mL activin A, 100 units/mL penicillin G, and 100 µg/mL streptomycin for 1 day, so that the cells were allowed to differentiate into the endoderm. Thereafter, the endoderm was cultured in DMEM/F12 supplemented with 2% FBS, 1% GlutaMAX, and 250 ng/mL FGF2 for 4 days, so that it was allowed to differentiate into intestinal stem cells.

(5) Culture and Subculture of Intestinal Stem Cells

Taking into consideration the previous reports, a maintenance medium comprising factors that were considered to be necessary for maintaining stem cell properties Advanced DMEM/F12 supplemented with 10% KSR, 100 units/mL penicillin G, 100 µg/mL streptomycin, 1% GlutaMAX, 5 µM Y-27632, 100 ng/mL EGF, 100 ng/mL Noggin, 100 ng/mL R-spondin 1, 100 ng/mL Wnt 3a, a fibroblast growth factor (5 ng/mL FGF2 or 100 ng/mL FGF4 or 100 ng/mL FGF10), 10 µM CHIR 99021, 1 mM valproic acid, 1 mg/mL nicotinamide, 1.5 µM A-83-01, 10 µM SB202190, and 1 mM N-Acetylcystein) was newly conceived, and was used in the present studies.

The intestinal stem cells differentiated from iPS cells were peeled from the culture dish using accutase, and were then suspended in a maintenance medium. Thereafter, the suspension was seeded on a 6- or 10-cm dish for cell culture that was coated with gelatin. This time point was defined as passage 1. With regard to medium exchange, the medium was exchanged with a medium formed by removing Y-27632 from the maintenance medium every 2 or 3 days. The subculture was initiated, when the percentage of the cells occupied with respect to the culture dish became approximately 80%. The culture solution was removed from the culture dish by aspiration, and was then washed with 5 mL D-PBS(−)/10 cm dish twice. The cell suspension was peeled from the culture dish using accutase, and was then recovered in a 15 mL centrifuge tube. For the subculture, a cell count of approximately 50% per dish before subculture was used, and a cell count of approximately 25% was used in the extraction of total ribonucleic acid (RNA). The cells to be subcultured were centrifuged at 1,000 rpm (160×g) for 3 minutes, and a supernatant was then removed by aspiration as much as possible. The resultant was suspended in a maintenance medium, and was then seeded on a gelatin-coated 6- or 10-cm dish for cell culture. Twenty-four hours after the subculture, the medium was exchanged with a medium that did not contain Y-27632.

(6) Differentiation of Intestinal Stem Cells into Intestinal Epithelial Cells

Differentiation of the intestinal stem cells into intestinal epithelial cells was initiated, when the percentage of the intestinal stem cells became approximately 80% with respect to the culture dish. The cells were peeled from the culture dish using accutase, and were then seeded on a 24-well plate for cell culture coated with Matrigel excluding growth factors, which had previously been 30-fold diluted with a medium for human iPS cells. Thereafter, the cells were cultured in DMEM/F12 supplemented with 2% FBS, 2 mmol/L L-Glu, 1% NEAA, 2% B27 supplement, 1% N2 supplement, 100 units/mL penicillin G, 100 µg/mL streptomycin, 20 ng/mL epidermal growth factor (EGF), and 10 µmol/L Y-27632 for 1 day, and were then cultured in DMEM/F12 supplemented with 2% FBS, 2 mmol/L L-Glu, 1% NEAA, 2% B27 supplement, 1% N2 supplement, 100 units/mL, penicillin G, 100 µg/mL streptomycin, and 20 ng/mL EGF for 18 days, so that the intestinal stem cells were allowed to differentiate into intestinal epithelial cells. Moreover, upon the differentiation, the low molecular weight compounds PD98059 (20 µmol/L), 5-aza-2'-deoxycytidine (5 µmol/L) and A-83-01 (0.5 µmol/L), which we had found before, were added.

(7) RNA Extraction

After completion of the recovery of intestinal stem cells at subculture and the recovery of intestinal epithelial cells after differentiation of the intestinal stem cells into the intestinal epithelial cells, RNA was extracted in accordance with the instruction manual included with Agencourt (registered trademark) RNAdvance™ issue Kit.

(8) Reverse Transcription Reaction

Complementary DNA (cDNA) was synthesized using ReverTra Ace (registered trademark) qPCR RT Master Mix, in accordance with the instruction manual included therewith.

(9) Real-Time Reverse Transcription Polymerase Chain Reaction (Real-Time RT-PCR)

Real-Time RT-PCR was carried out on the cDNA used as a template, using KAPA SYBR Fast qPCR Kit, in accordance with the instruction manual included therewith. The results were corrected using, as an endogenous control, glyceraldehyde-3-phosphate dehydrogenase (GAPDH).

Besides, for the evaluation of stem cell properties, LGR5 (a leucine rich repeat-containing G protein conjugated receptor, as a marker of intestinal stem cells) and SOX9 (an intestinal tract progenitor cell marker) were utilized, whereas for the evaluation of differentiation of the cells into intestinal tract epithelium-like cells, villin 1 (as a main constituent of microvilli), sucrase-isomaltase (a disaccharide decomposing enzyme present in the intestinal tract epithelium), as a marker specific to the intestinal tract epithelium), PEPT1 (SLC (solute carrier) family member 15A1/peptide transporter 1, expressed on the apical membrane side of the small intestine), and MDR1 (ATP-binding cassette transporter B1/multidrug resistance protein 1, P glycoprotein, efflux transporter) were utilized.

Figure 1:
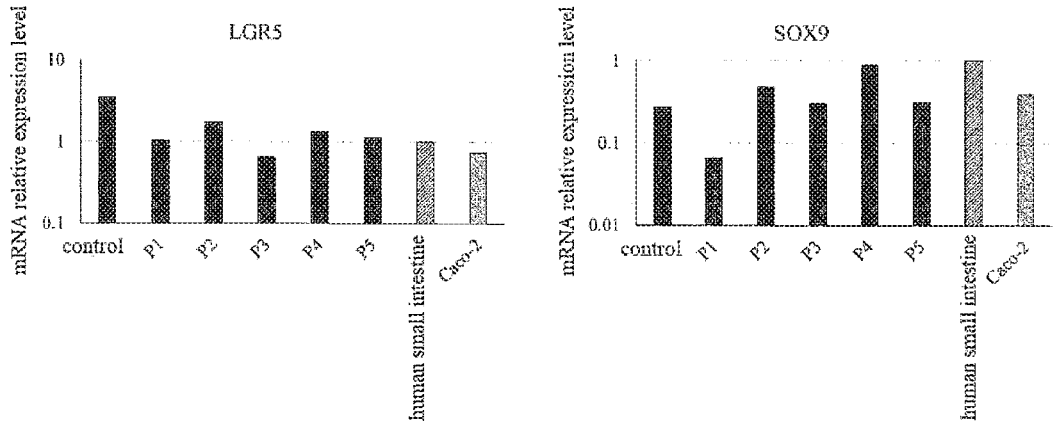
FIG. 1 shows the expression of an intestinal stem cell-related gene in the maintenance culture of intestinal stem cells that have been differentiated from human iPS cells. The figure shows the results in the case of adding FGF2 to the medium. Intestinal stem cells that have been differentiated from human iPS cells (not-passaged) were used as a control.
Figure 2:
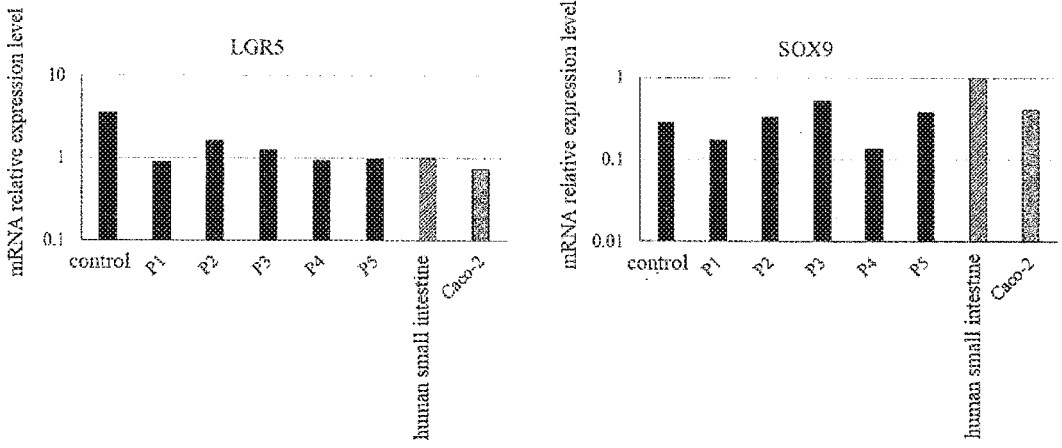
FIG. 2 shows the expression of intestinal stem cell-related gene in the maintenance culture of intestinal stem cells that have been differentiated from human iPS cells. The figure shows the results in the case of adding FGF4 to the medium. Intestinal stem cells that have been differentiated from human iPS cells (not-passaged) were used as a control.
Figure 3:
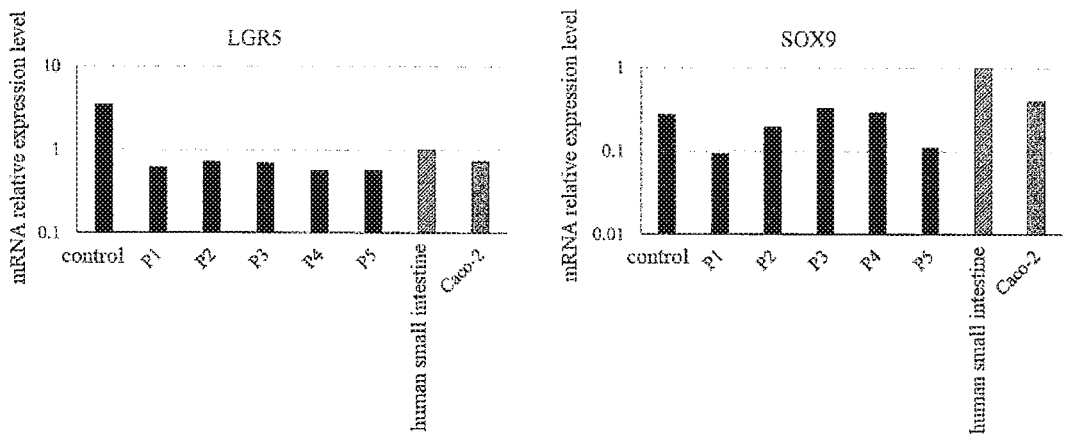
FIG. 3 shows the expression of intestinal stem cell-related gene in the maintenance culture of intestinal stem cells that have been differentiated from human iPS cells. The figure shows the results in the case of adding FGF10 to the medium. Intestinal stem cells that have been differentiated from human iPS cells (not-passaged) were used as a control.

2. Results and/or Consideration (1) Studies Regarding Culture Method of Intestinal Stem Cells The influence of the newly conceived maintenance medium on the maintenance of stem cell properties and the influence of fibroblast growth factors (FGF2, FGF4, and FGF10) added at that time were studied by performing a subculture. As a result, the mRNA expression level of LGR5 as a marker of stem cell properties and SOX9 as a progenitor cell marker was confirmed to be equivalent, in comparison to the human small intestine (FIGS. 1 to 3). In addition, a slight fluctuation and attenuation in the expression level were confirmed, but in comparison to the human small intestine, the expression level was maintained at an equivalent level (FIGS. 1 to 3). A great difference was not observed regarding the fibroblast growth factors. These results show that the subculture of intestinal stem cells can be carried out using the newly conceived maintenance medium. A great difference was not observed among the fibroblast growth factors (FGF2, FGF4, and FGF10) added into the maintenance medium.

(2) Studies Regarding Differentiation of Intestinal Stem Cells

Figure 4:
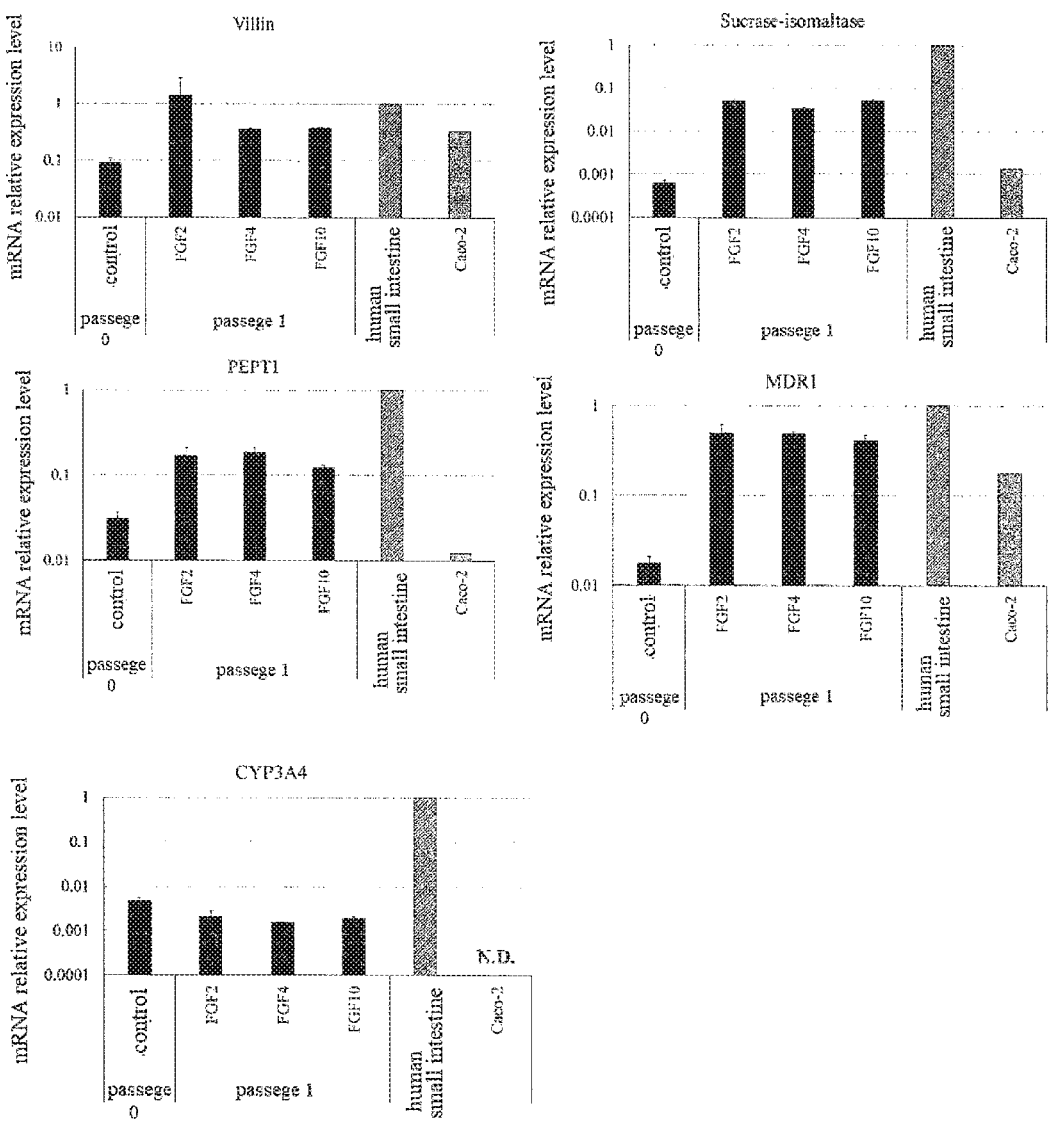
FIG. 4 shows the expression level of mRNA of various types of marker genes in intestinal epithelial cells that have been differentiated from intestinal stem cells. The results are shown as a mean value±S.D. (n=3). As a control, a group, in which intestinal stem cells have been differentiated without being subjected to maintenance culture, was used.

A comparison was made in terms of the mRNA expression levels of intestinal epithelial markers and pharmacokinetics-related genes, between a case where the iPS cells were allowed to differentiate into the intestinal stem cells, which were then allowed to differentiate into intestinal epithelial cells without performing subcultures (control), and a case where the iPS cells were allowed to differentiate into the intestinal stem cells, which were then subcultured once and were then subjected to a maintenance culture according to the method of culturing intestinal stem cells established by the present studies (an FGF2 addition maintenance group, an FGF4 addition maintenance group, and an FGF10 addition maintenance group), which were further allowed to differentiate into intestinal epithelial cells. As a result, in the group in which the maintenance culture was performed, the mRNA expression level of villin was increased by 4.1 to 15.8 times, the mRNA expression level of sucrase-isomaltase was increased by 53.6 to 86.2 times, the mRNA expression level of PEPT1 was increased by 4.0 to 6.1 times, and the mRNA expression level of MDR1 was increased by 23.4 to 28.0 times, in comparison to the control (FIG. 4).

As described above, by using the newly conceived maintenance medium, it became possible to culture intestinal stem cells differentiated from human iPS cells, while maintaining the properties of the intestinal stem cells. Moreover, surprisingly, when the intestinal stem cells that had been subjected to a maintenance culture were allowed to differentiate into intestinal epithelial cells, the mRNA expression levels of intestinal epithelial markers and pharmacokinetics-related genes in the intestinal epithelial cells were significantly increased, in comparison to the control. These results show that the successfully established maintenance culture method of human iPS cell-derived intestinal stem cells is useful not only as a means for the mass proliferation of intestinal stem cells or the long-term maintenance thereof, but also for promotion of the differentiation into intestinal epithelial cells and the improvement of functions.

B. Studies Regarding Properties of Human iPS Cell-Derived Intestinal Epithelial Cells In order to further study the usefulness of iPS cell-derived intestinal epithelial cells, attention has been paid to mucin 2 that is a mucosal material associated with protection of the intestinal tract mucous membrane and CgA that is focused as an indicator of stress, and the expression state of these substances in iPS cell-derived intestinal epithelial cells has been examined.

1. Method iPS cells were allowed to differentiate into intestinal stem cells, which were then subcultured once. Thereafter, the cells were subjected to a maintenance culture according to the culture method of intestinal stem cells, which had been established in the above-described studies, and were then allowed to differentiate into intestinal epithelial cells.

(1) Detection of Mucin 2

In the process of allowing the intestinal stem cells to differentiate into the intestinal epithelial cells, indomethacin (50 µM and 200 µM) and rebamipide (50 µM, 100 µM and 200 µM) were added into the medium for 6 days, and the influence of these substances on the expression of mucin 2 was then examined.

<RNA Extraction>

After the differentiated intestinal epithelial cells had been recovered, RNA was extracted using Agencourt (registered trademark) RNAdvance™ Tissue Kit, in accordance with the instruction manual included therewith.

<Reverse Transcription Reaction>

Complementary DNA (cDNA) was synthesized using ReverTra Ace (registered trademark) qPCR RT Master Mix, in accordance with the instruction manual included therewith.

<Real-Time Reverse Transcription Polymerase Chain Reaction (Real-Time RT-PCR)>

Real-Time RT-PCR was carried out on cDNA used as a template, using KAPA SYBR Fast qPCR Kit, in accordance with the instruction manual included therewith. The results were corrected using hypoxanthine-guanine phosphoribosyltransferase (HPRT) as an endogenous control.

(2) Detection of CgA

In the process of allowing the intestinal stem cells to differentiate into the intestinal epithelial cells, indomethacin (50 µM and 200 µM) and rebamipide (50 µM, 100 µM, and 200 µM) were added into the medium for 6 days, and the influence of these substances on the expression of CgA was then examined.

<RNA Extraction>

After the differentiated intestinal epithelial cells had been recovered, RNA was extracted using Agencourt (registered trademark) RNAdvance™ Tissue Kit, in accordance with the instruction manual included therewith.

<Reverse Transcription Reaction>

Complementary DNA (cDNA) was synthesized using ReverTra Ace (registered trademark) qPCR RT Master Mix, in accordance with the instruction manual included therewith.

<Real-Time Reverse Transcription Polymerase Chain Reaction (Real-Time RT-PCR)>

Real-Time RT-PCR was carried out on cDNA used as a template, using KAPA SYBR Fast qPCR Kit, in accordance with the instruction manual included therewith. The results were corrected using hypoxanthine-guanine phosphoribosyltransferase (HPRT) as an endogenous control.

2. Results and Consideration (1) Expression of Mucin 2 and Change Thereof

Figure 5:
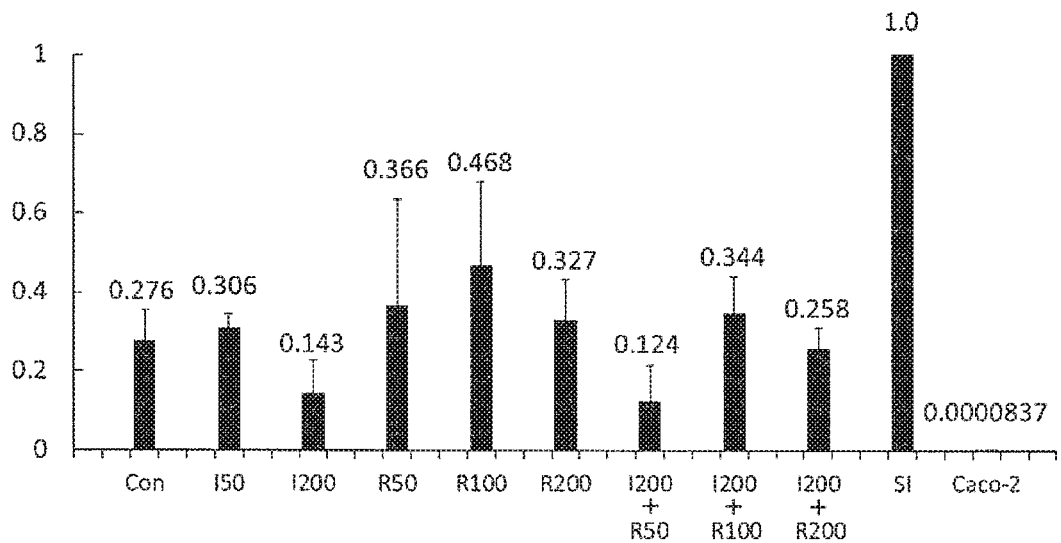
FIG. 5 shows the expression of mucin 2 (at an mRNA level) in intestinal epithelial cells that have been differentiated from intestinal stem cells, and the results of an assay using the same. The longitudinal axis indicates a relative value obtained using the expression level of commercially available human small intestinal cells (SI) as a reference (1).

The detection results of mucin 2 mRNA are shown in FIG. 5. The intestinal epithelial cells (Con) prepared by the present method highly expressed mucin 2, which was hardly expressed in human colon cancer-derived Caco-2 cells (Caco-2). The expression level of mucin 2 in the present intestinal epithelial cells reached approximately 30% of the expression level of mucin 2 in commercially available human small intestine-derived cells (SI). This fact shows that the intestinal epithelial cells prepared by the present method are extremely highly valuable as a small intestine model system.

When indomethacin was added in a concentration of 200 µM to the medium, the expression of mucin 2 (mRNA expression level) in the intestinal epithelial cells prepared by the present method was decreased (I200). On the other hand, when rebamipide was added into the medium (50 µM, 100 µM, and 200 µM), the expression level of mucin 2 (mRNA expression level) was increased (R50, R100, and R200). Besides, when rebamipide was added in a concentration of 200 µM to the medium (R200), too high concentration was likely to cause cytotoxicity. When both indomethacin (200 µM) and rebamipide (100 µM or 200 µM) were added into the medium, a decrease in the expression of mucin 2 (mRNA expression level) tended to be suppressed (I200+R100, I200+R200). The aforementioned results show that the intestinal epithelial cells prepared by the present method are useful for assays using the expression of mucin 2 as an indicator (specifically, prediction of a drug causing mucous membrane disorder (ulcer) as a side effect (prediction of the risk of causing side effects) and a screening system for a drug having an action to suppress such side effects or stress ulcer).

(2) Expression of CgA and Change Thereof

The detection results of CgA mRNA are shown in FIG. 6. The intestinal epithelial cells prepared by the present method (Con) expressed CgA at a level incomparable to human colon cancer-derived Caco-2 cells (Caco-2). This fact also demonstrates that the intestinal epithelial cells prepared by the present method are extremely highly valuable as a small intestine model system.

When indomethacin was added into the medium (50 µM and 200 µM), the expression level of CgA (mRNA expression level) in the intestinal epithelial cells prepared by the present method was decreased (I50, I200). On the other hand, when rebamipide was added into the medium (50 µM, 100 µM, and 200 µM), an increase in the expression level of CgA (mRNA expression level) was not particularly observed (R50, R100, and R200). However, when both indomethacin (200 µM) and rebamipide (100 µM or 200 µM) were added into the medium, a decrease in the expression level of CgA (mRNA expression level) tended to be suppressed (I200+R100 and I200+R200). The aforementioned results show that the intestinal epithelial cells prepared by the present method are useful for assays using the expression of CgA as an indicator (specifically, prediction of a drug causing mucous membrane disorder (ulcer) as a side effect (prediction of the risk of causing side effects) and a screening system for a drug having an action to suppress such side effects or stress ulcer).

C. Development 2 of Novel Culture Method of Human iPS Cell-Derived Intestinal Stem Cell-Like Cells Aiming for improving the culture method of human iPS cell-derived intestinal stem cell-like cells, factors to be added into the medium were changed, and the influence/effects thereof were then examined. Specifically, using Advanced DMEM/F12 supplemented with 10% KSR, 100 units/mL penicillin G, 100 μg/mL streptomycin, 1% Gluta-MAX, 2 μM Y-27632, 100 ng/mL EGF, 30 ng/mL FGF2, 3 μM CHIR 99021, and 0.5 μM A-83-01, human iPS cells were allowed to differentiate into intestinal stem cells. Thereafter, the obtained intestinal stem cells were subcultured, and using the expression level of markers (LGR5: small intestine stem cell marker, and CDX2: hindgut marker) as an indicator, whether the stem cell properties were maintained were evaluated. Other than the medium conditions, the same conditions as those in the case of the above A were applied. In addition, the used cells (human iPS cells and MEF), the method of culturing human iPS cells, etc. were also the same as those in the case of the above A. It is to be noted that the number of factors added into the medium used in the present studies was significantly smaller than that in the medium used in the above studies A, and that the medium used in the present studies is particularly characterized in that valproic acid as a histone deacetylation inhibitor was not added thereto.

The experimental results are shown in FIG. 7. Even if the subculture was repeatedly carried out (P1 to P11), the mRNA expression level of LGR5 serving as a marker of stem cell properties and that of CDX2 serving as a hindgut marker were equivalent to or higher than that in the human small intestine, and it was demonstrated that the above-described medium is extremely effective for the maintenance (subculture) of human iPS cell-derived intestinal stem cell-like cells.

The human iPS cell-derived intestinal stem cell-like cells before subculture (P0) and after subcultures (P1 to P10) were allowed to differentiate into intestinal epithelial cells (wherein the method was the same as that in the above A), and the expression of various types of markers (villin: an intestinal tract marker, sucrase-isomaltase: an intestinal tract marker, ISX: an intestinal tract marker, LGR5: an intestinal stem cell marker, MDR1: a transporter gene, PEPT1: a transporter gene, and CYP3A4: a drug-metabolizing enzyme gene) was then examined. The results are shown in FIGS. 8 and 9. Even in a case where the subcultured cells were allowed to differentiate into intestinal epithelial cells, the high expression of the intestinal epithelial markers and the pharmacokinetics-related genes was observed. The expression level of villin 1, ISX, MDR1, and the like tended to be increased, as the subculture was repeatedly carried out, and higher expression was observed than that in the human small intestine.

As described above, it was confirmed that a maintenance culture method using the above-described medium is extremely effective for the maintenance (culture) of human iPS cell-derived intestinal stem cell-like cells, and promotion of differentiation of the cells into intestinal epithelial cells and the improvement of functions.

INDUSTRIAL APPLICABILITY

The culture method of the present invention enables mass preparation of iPS cell-derived intestinal stem cell-like cells and the maintenance thereof over a long period of time. Moreover, by preparing the iPS cell-derived intestinal epithelial cell-like cells by the culture method of the present invention, more mature intestinal epithelial cell-like cells can be obtained. The intestinal epithelial cell-like cells are useful as a small intestine model system, and can be utilized in the evaluation of absorption and/or metabolism, membrane permeability, induction of a drug-metabolizing enzyme, induction of a drug transporter, toxicity, etc. Furthermore, it can also be expected that the intestinal epithelial cell-like cells are utilized as an active ingredient of a cell preparation for use in treating various types of intestinal diseases, or as a material for regenerative medicine. Further, it can also be expected that the present invention will contribute to clarification of the functions of intestinal stem cells, clarification of the developmental process of the intestinal tract, clarification of the cause of gastrointestinal disease or progression mechanism thereof, etc.

The above-described embodiments and examples of the invention are not intended to limit the present invention. Various modifications may also be included in the present invention, unless the modifications are deviated from the description of the claims, within a range in which a person skilled in the art could readily have conceived of the modifications. The study papers, published patent publications, patent publications, etc., which are explicitly disclosed in the present description, are incorporated herein by reference in their entirety.

The invention claimed is:

1. A method for culturing induced pluripotent stem cell-derived intestinal stem cell-like cells, which comprises a step of culturing induced pluripotent stem cell-derived intestinal stem cell-like cells in the presence of a GSK-3β inhibitor, a histone deacetylation inhibitor, a TGFβ receptor inhibitor, a fibroblast growth factor, and a serum replacement, or in the presence of a GSK-3β inhibitor, a TGFβ receptor inhibitor, a fibroblast growth factor, and a serum replacement, wherein properties of the induced pluripotent stem cell-derived intestinal stem cell-like cells are maintained.

2. The method according to claim 1, wherein the GSK-3β inhibitor is CHIR 99021, SB216763, CHIR 98014, TWS119, Tideglusib, SB415286, BIO, AZD2858, AZD1080, AR-A014418, TDZD-8, LY2090314, IM-12, Indirubin, Bikinin or 1-Azakenpaullone, the histone deacetylation inhibitor is valproic acid, vorinostat, trichostatin A, tubastatin A, givinostat or pracinostat, and the serum replacement is a knockout serum replacement.

3. The method according to claim 1, wherein the culture is carried out under conditions in which an epidermal growth factor is further present.

4. The method according to claim 1, wherein the TGFβ receptor inhibitor is A-83-01, and the fibroblast growth factor is FGF2, FGF4 or FGF10.

5. The method according to claim 1, wherein the culture is carried out under conditions in which one or more compounds selected from the group consisting of a BMP inhibitor, a Wnt signaling activator and a Wnt agonist are further present.

6. The method according to claim 5, wherein the BMP inhibitor is Noggin, the Wnt signaling activator is R-spondin 1, and the Wnt agonist is Wnt3a.

7. The method according to claim 1, wherein the culture is carried out under conditions in which one or more compounds selected from the group consisting of nicotinamide, N-acetylcysteine, a p38 inhibitor and a ROCK inhibitor are further present.

8. The method according to claim 7, wherein the p38 inhibitor is SB202190, and the ROCK inhibitor is Y-27632.

9. The method according to claim 1, wherein the induced pluripotent stem cells are human induced pluripotent stem cells.

10. A method for preparing intestinal epithelial cell-like cells, which comprises:
 culturing induced pluripotent stem cell-derived intestinal stem cell-like cells by the method according to claim 1, and
 allowing the thus-obtained intestinal stem cell-like cells to differentiate into intestinal epithelial cell-like cells.

\* \* \* \* \*